United States Patent
Nemoto et al.

(10) Patent No.: US 11,020,532 B2
(45) Date of Patent: Jun. 1, 2021

(54) INJECTING APPARATUS AND REAR END DETECTION DEVICE

(71) Applicant: NEMOTO KYORINDO CO., LTD., Tokyo (JP)

(72) Inventors: Shigeru Nemoto, Tokyo (JP); Kousuke Nakagawa, Tokyo (JP); Hirofumi Uchizono, Tokyo (JP)

(73) Assignee: NEMOTO KYORINDO CO., LTD., Tokyo (JP)

( * ) Notice: Subject to any disclaimer, the term of this patent is extended or adjusted under 35 U.S.C. 154(b) by 1150 days.

(21) Appl. No.: 15/119,207

(22) PCT Filed: Feb. 20, 2015

(86) PCT No.: PCT/JP2015/000822
§ 371 (c)(1),
(2) Date: Aug. 16, 2016

(87) PCT Pub. No.: WO2015/129227
PCT Pub. Date: Sep. 3, 2015

(65) Prior Publication Data
US 2017/0007772 A1  Jan. 12, 2017

(30) Foreign Application Priority Data
Feb. 28, 2014  (JP) .............................. JP2014-038269

(51) Int. Cl.
*A61M 5/315* (2006.01)
*A61M 5/145* (2006.01)
(Continued)

(52) U.S. Cl.
CPC ........ *A61M 5/31515* (2013.01); *A61M 5/007* (2013.01); *A61M 5/1456* (2013.01);
(Continued)

(58) Field of Classification Search
CPC ........ A61M 2205/3306; A61M 5/1456; A61M 5/1458; A61M 5/31515; A61M 2005/3152; A61M 5/007; A61M 5/14546
See application file for complete search history.

(56) References Cited

U.S. PATENT DOCUMENTS 9,358,336 B2  6/2016  Munk et al.
2007/0074596 A1 *  4/2007  Siefert ................ A61M 5/1456
74/441

FOREIGN PATENT DOCUMENTS

JP  2003-220136 A  8/2003
JP  2003220136    *  8/2003
(Continued)

OTHER PUBLICATIONS

Shigeru et al., Medicine-Injecting Device, Syringe Adapter, Injection Head, EPO translation (Year: 2003).*
(Continued)

*Primary Examiner* — Laura A Bouchelle
(74) *Attorney, Agent, or Firm* — Studebaker & Brackett PC

(57) ABSTRACT

A pushing unit is stopped just before abutting against a rear end of a syringe to reliably prevent unwanted extrusion of a chemical liquid from a syringe. An injecting apparatus for injecting a chemical liquid includes: an injection head to which a syringe filled with the chemical liquid is to be mounted; a pushing unit provided on the injection head and pushing a rear end of the syringe; a rear end detection unit provided on the injection head and detecting the rear end in a contactless manner; and a control unit configured to control the injection head, the control unit acquiring a forward movement distance that the pushing unit is to be moved forward after the rear end is detected, and causing the pushing unit to move forward by the forward movement
(Continued)

distance after the rear end is detected and to stop at a position separated from the rear end.

8 Claims, 18 Drawing Sheets

(51) Int. Cl.
    *A61M 5/00*     (2006.01)
    *A61M 5/20*     (2006.01)

(52) U.S. Cl.
    CPC ...... *A61M 5/1458* (2013.01); *A61M 5/14546* (2013.01); *A61M 5/2033* (2013.01); *A61M 2005/3152* (2013.01); *A61M 2205/14* (2013.01); *A61M 2205/3306* (2013.01)

(56) References Cited

FOREIGN PATENT DOCUMENTS

| | | |
|---|---|---|
| JP | 2009-503373 A | 1/2009 |
| WO | 2005/102416 A1 | 11/2005 |
| WO | 2008/123524 A1 | 10/2008 |
| WO | 2013/129570 A1 | 9/2013 |
| WO | 2013/144152 A1 | 10/2013 |
| WO | WO2013144152 * | 10/2013 |

OTHER PUBLICATIONS

International Search Report issued in PCT/JP2015/000822; dated Apr. 28, 2015.
Written Opinion issued in PCT/JP2015/000822; dated Apr. 28, 2015.
Extended European Search Report (EESR) dated Feb. 9, 2017 from corresponding EP Appl No. 15754443.8, 7 pp.
Notification of Transmittal of Copies of Translation of the International Preliminary Report on Patentability and Translation of Written Opinion of the International Searching Authority; PCT/JP2015/000822 dated Sep. 6, 2016.

* cited by examiner

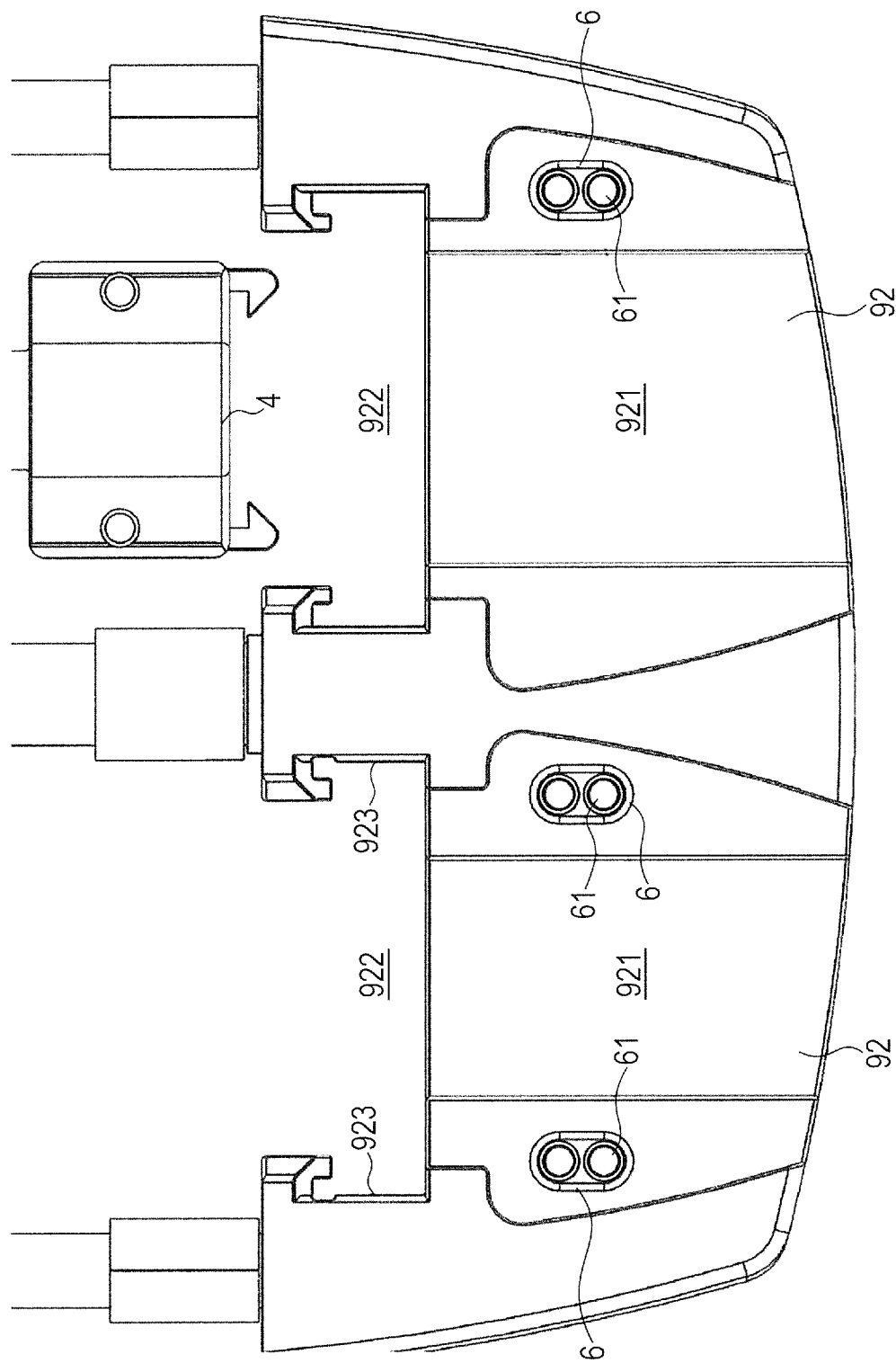

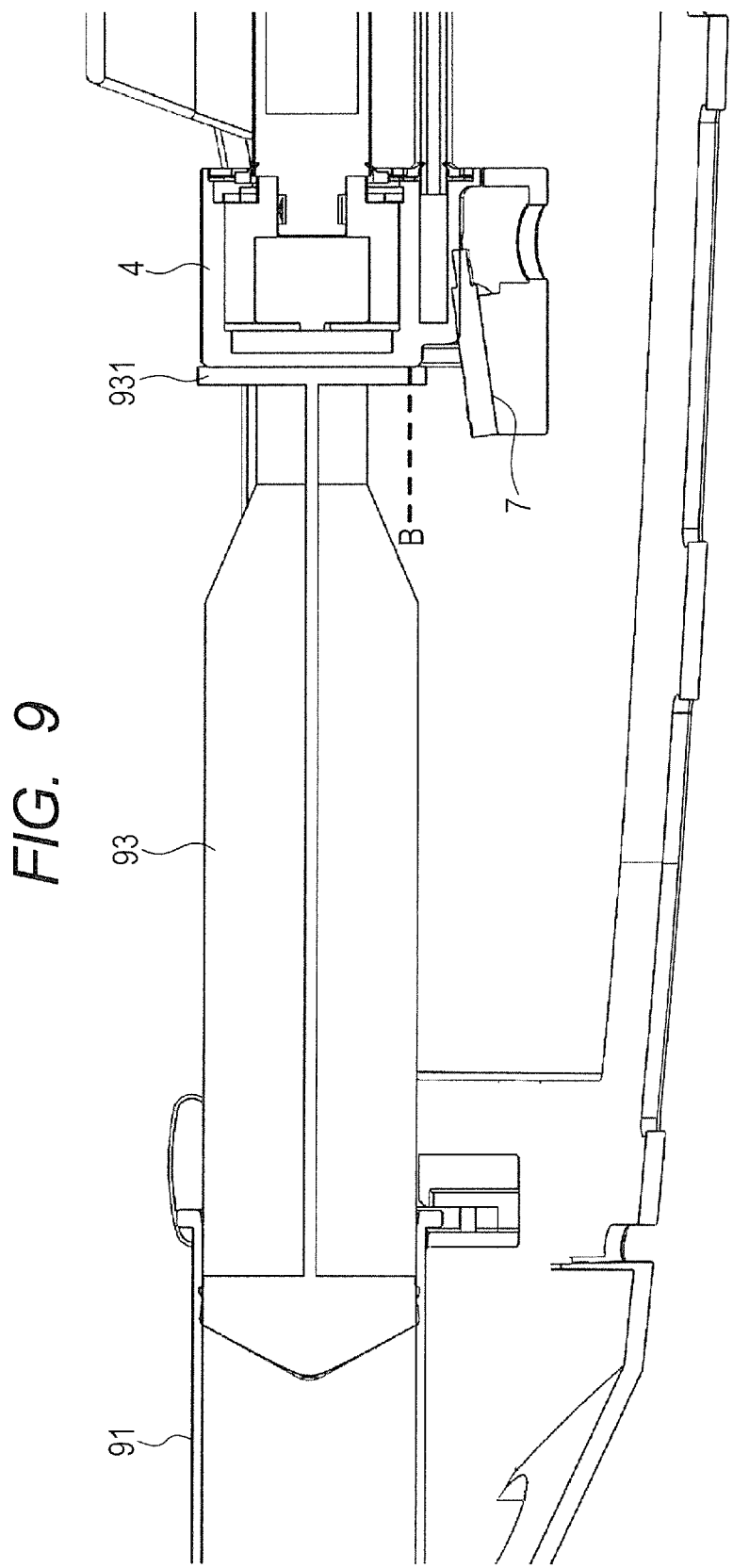

INJECTING APPARATUS AND REAR END DETECTION DEVICE

TECHNICAL FIELD

The present invention relates to a rear end detection device configured to detect a rear end of a syringe, and an injecting apparatus including the rear end detection device.

BACKGROUND ART

In Patent Literature 1, there is described an injecting apparatus including a piston drive mechanism having a piston pushing unit configured to push an end of a piston, and a proximity sensor configured to detect a distance between the piston and the piston pushing unit. The piston pushing unit is controlled based on a detection result of the distance by the proximity sensor so as to move from an initial position until abutting against the end of the piston.

CITATION LIST

Patent Literature

PTL 1: WO 2013/129570 A1

SUMMARY OF INVENTION

Technical Problem

In the injecting apparatus described in Patent Literature 1, the piston pushing unit is configured to move until the piston pushing unit abuts against the end of the piston. As a result, the piston pushing unit may slightly push the piston, and thus a small amount of a chemical liquid may be extruded from a syringe. In such a case, the amount of the filled chemical liquid changes, and hence the syringe may need to be replaced with a new syringe.

Solution to Problem

In order to solve the above-mentioned problem, according to one embodiment of the present invention, there is provided an injecting apparatus for injecting a chemical liquid, the injecting apparatus including: an injection head to which a syringe filled with the chemical liquid is to be mounted; a pushing unit provided on the injection head and pushing a rear end of the syringe; a rear end detection unit provided on the injection head and detecting the rear end in a contactless manner; and a control unit configured to control the injection head, the control unit acquiring a forward movement distance that the pushing unit is to be moved forward after the rear end is detected, and causing the pushing unit to move forward by the forward movement distance after the rear end is detected and to stop at a position separated from the rear end.

According to another embodiment of the present invention, there is provided a rear end detection device, including: a rear end detection unit provided on an injection head, to which a syringe filled with a chemical liquid is to be mounted, and detecting a rear end of the syringe in a contactless manner; a holding unit holding the rear end detection unit; and the rear end detection unit including a light emitting portion and a light receiving portion, and the light emitting portion and the light receiving portion which are held by a pushing unit so as to protrude in front of the pushing unit.

As a result, the forward movement of the pushing unit can be stopped just before the pushing unit abuts against the rear end of the syringe. This enables unwanted extrusion of the chemical liquid from the syringe to be reliably prevented.

Further features of the present invention will become apparent from the following description of exemplary embodiments referring to the attached drawings.

BRIEF DESCRIPTION OF DRAWINGS

FIG. 3 is a schematic top view of a front end portion of an injection head.

FIG. 9 is a schematic cross-sectional view of the front-side portion of the injection head.

DESCRIPTION OF EMBODIMENTS

Exemplary embodiments for carrying out the present invention are now described in detail with reference to the drawings. However, the dimensions, materials, shapes, and relative positions of the components, etc., described in the following embodiments may be freely set. They may be changed based on the configuration of the device to which the present invention is applied or based on various conditions. Unless noted otherwise, the scope of the present invention is not limited to the embodiments specifically described herein. "Upward" and "downward" herein respectively correspond to the upward direction and the downward direction in the direction of gravity. Further, the front side corresponds to the side on which the syringe is mounted in the injecting apparatus, and the rear side corresponds to the opposite side to the front side.

First Embodiment

Figure 1:
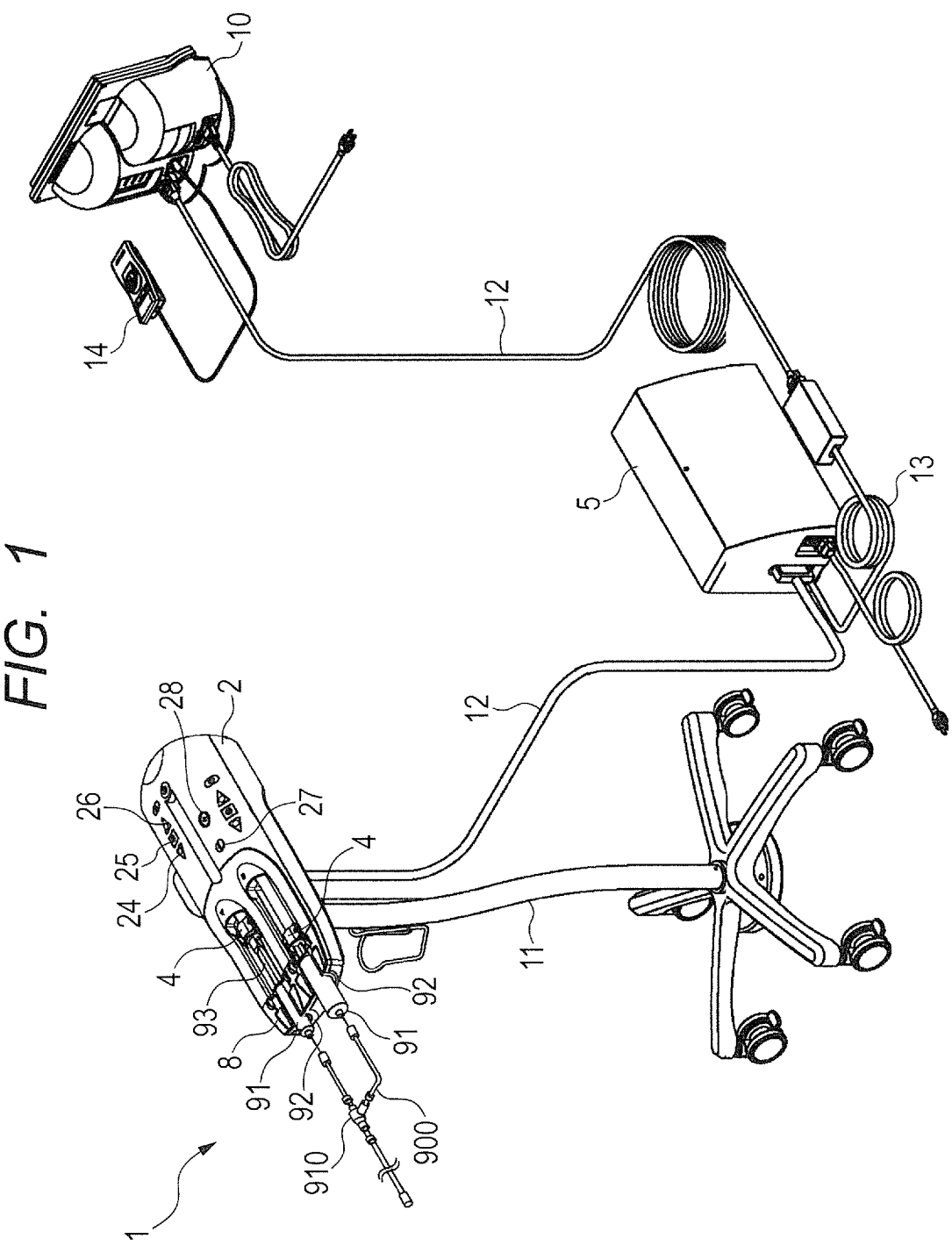
FIG. 1 is a schematic perspective view of an injecting apparatus according to a first embodiment of the present invention.
Figure 2:
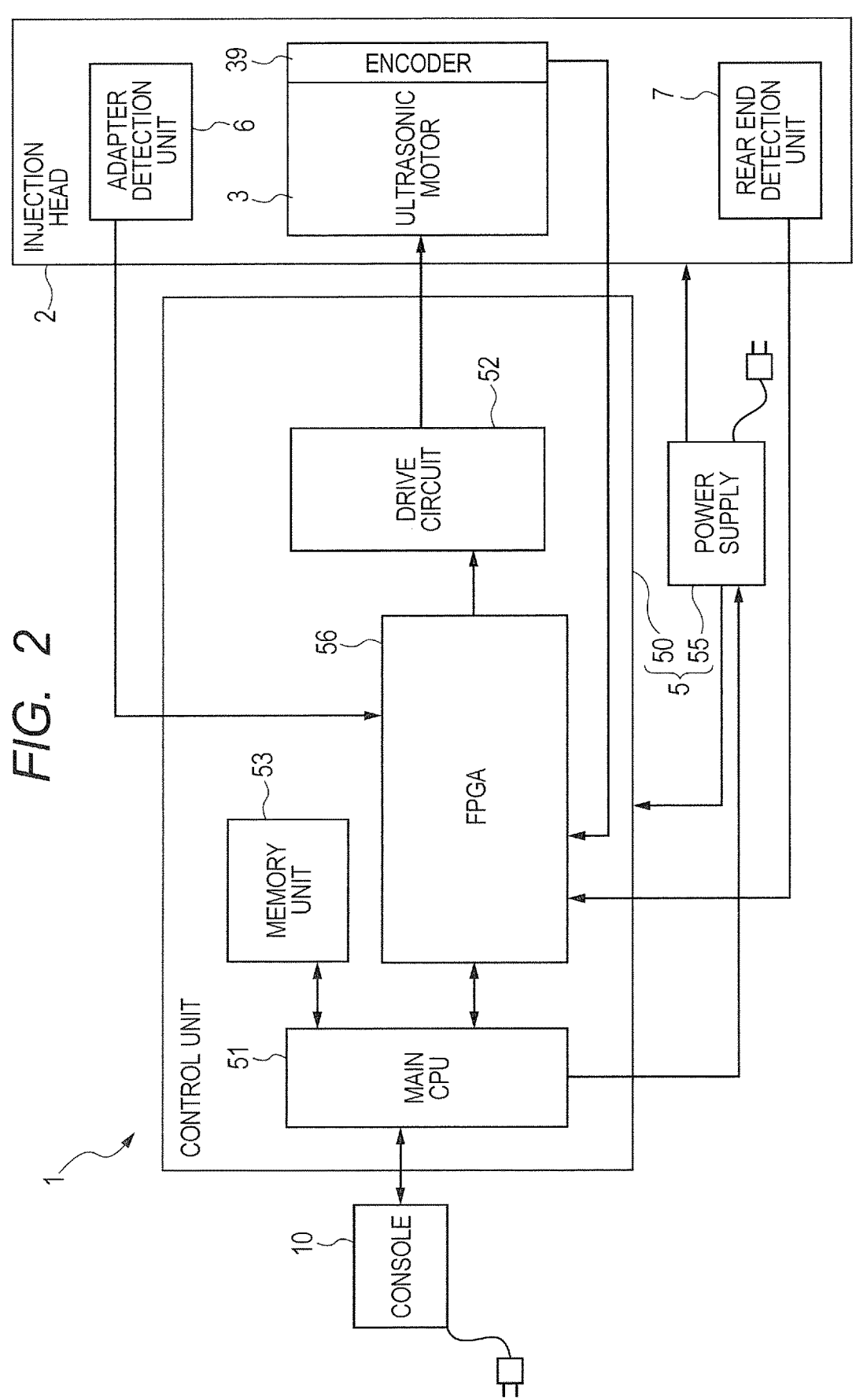
FIG. 2 is a schematic block diagram of the injecting apparatus according to the first embodiment.

FIG. 1 is a schematic perspective view of an injecting apparatus 1. FIG. 2 is a schematic block diagram of the injecting apparatus 1. As illustrated in FIG. 1 and FIG. 2, the injecting apparatus 1, which is for injecting a chemical liquid, includes: an injection head 2, to which a syringe 91 filled with the chemical liquid is to be mounted; a pushing unit 4, which is provided on the injection head 2 and which is configured to push a rear end 931 (FIG. 9) of a piston 93 as a rear end of the syringe 91; a rear end detection unit 7, which is provided to the injection head 2 and which serves as a rear end detection device configured to detect the rear end 931 in a contactless manner; and a control device 5 including a control unit 50 configured to control the injection head 2.

The pushing unit 4 is controlled by the control unit 50 so as to move forward and push the rear end 931 of the piston 93 in order to discharge the chemical liquid in the syringe 91. Specifically, the control unit 50 is configured to control an ultrasonic motor 3 provided in the injection head 2 such that the pushing unit 4 moves forward when the ultrasonic motor 3 is rotating normally and moves backward when the ultrasonic motor 3 is rotating in reverse. The rear end detection unit 7 is configured to detect the rear end 931 of the piston 93 as the rear end of the syringe 91.

The injecting apparatus 1 also includes an adapter 8 for mounting the syringe 91 to the injection head 2, and adapter detection units 6 as adapter detection devices configured to detect the adapter 8. The adapter 8 is attached to a syringe holder 92 for mounting the syringe 91.

The injecting apparatus 1 is connected to an imaging apparatus (not shown) by a cable or wirelessly. During injection of the chemical liquid and during image taking, various kinds of data are transmitted and received to and from the imaging apparatus and the injecting apparatus 1. For example, an imaging condition can be set or displayed on the injecting apparatus 1. The injection condition may also be set or displayed on the imaging apparatus. Examples of the imaging apparatus include various medical imaging apparatus, such as a magnetic resonance imaging (MRI) apparatus, a computed tomography (CT) apparatus, an angiographic imaging apparatus, a positron emission tomography (PET) apparatus, a single photon emission computed tomography (SPECT) apparatus, a CT angiographic apparatus, an MR angiographic apparatus, an ultrasonic diagnostic apparatus, and a vascular imaging apparatus.

The injecting apparatus 1 includes a console 10, which includes a touch panel as a display on which an injection state of the chemical liquid, for example, is displayed, and the control device 5, which includes the control unit 50 and a power supply 55 for the injection head 2. The console 10, the control device 5, and the injection head 2 may be connected to each other by a cable or wirelessly. For example, the console 10, the control device 5, and the injection head 2 may be connected to each other via a metal cable 12 and an optical cable 13, or may be wirelessly connected to each other by using a frequency band of 2.4 GHz to 5 GHz. Further, a remote operation device, e.g., a hand switch 14, may be connected to the console 10 by a cable or wirelessly. The remote operation device may also be connected to the injection head 2 by a cable or wirelessly, and be configured to start or stop a chemical liquid injection.

The control device 5 and the injection head 2 may be integrally formed with a caster stand 11. The control device 5 and the injection head 2 may also each be provided and mounted separately on the caster stand 11. Further, a ceiling member may be provided in place of the caster stand 11, and the injection head 2 may be hung from the ceiling via the ceiling member. The power supply 55 may also be provided in the injection head 2 or in the console 10. Further, an independent power supply 55 may also be provided separately. In addition, a battery may be used in place of the power supply 55.

Data of an operation pattern (injection protocol), data of the chemical liquid, and other such data are stored in advance in the console 10. When injecting the chemical liquid into a patient, an operator operates the touch panel or input buttons to input, for example, the injection protocol, e.g., an injection rate, an injection amount, an injection time, and a maximum injection pressure, physical data of the patient, e.g., a weight, a height, a body surface area, a heart rate, and a cardiac output, and data of the type of chemical liquid. The console 10 is configured to calculate an optimum injection condition based on the input data and the data stored in advance. Then, the console 10 is configured to determine the amount of the chemical liquid to be injected into the patient and the injection protocol based on the calculated injection condition.

The console 10 is configured to transmit, when the injection protocol, e.g., the injection amount, the injection rate, and the maximum injection pressure, of the chemical liquid has been determined, the injection protocol to the control device 5. The control device 5 is configured to temporarily store the received injection protocol. Information such as predetermined data or a graph is displayed on at least one of the touch panel or a display unit of the console 10, or a head display (not shown) of the injection head 2. Further, the information such as data or a graph may also be displayed on a portable display or a tablet computer, for example. Those devices, which are wirelessly connected to the injection head 2 or the control device 5 based on a standard such as Bluetooth (trademark) or Wi-Fi, may be used in place of the head display of the injection head 2. As a result, the operator can verify the displayed data or graph, for example. The data of the operation pattern (injection protocol), the data of the chemical liquid, and other such data may also be input from an external storage medium. The control device 5 is connected to the ultrasonic motor 3, and an encoder 39 is connected to the ultrasonic motor 3. The encoder 39 is configured to transmit to the control device 5 a pulse signal of a frequency corresponding to a rotational speed of the ultrasonic motor 3.

The pushing unit 4 includes a drive mechanism (not shown). The drive mechanism includes a transmission mechanism connected to a shaft of the ultrasonic motor 3, a screw shaft connected to the transmission mechanism, a trapezoidal screw nut screwed on the screw shaft, and an actuator connected to the trapezoidal screw nut. The transmission mechanism includes a pinion gear connected to the shaft and a screw gear connected to the screw shaft. The transmission mechanism is configured to transmit rotation from the ultrasonic motor 3 to the screw shaft. The rotation of the shaft of the ultrasonic motor 3 is transmitted to the screw shaft via the pinion gear and the screw gear. As a result, the screw shaft rotates based on the transmitted rotation. The trapezoidal screw nut is configured to slide in a forward movement direction or a backward movement direction in conjunction with the rotation of the screw shaft. A front end portion of the pushing unit 4 moves forward or moves backward in conjunction with the sliding of the trapezoidal screw nut.

The piston 93, which is capable of sliding in the syringe 91, is attached to the syringe 91. When the ultrasonic motor 3 is rotated normally under a state in which the rear end 931 of the piston 93 abuts against the pushing unit 4, the pushing unit 4 pushes the piston 93 in the forward movement direction. When the piston 93 moves forward, the chemical liquid in the syringe 91 is extruded, and is injected into the body of the patient via, for example, an extension tube 900 connected to a tip end of the syringe 91 and a mixing device 910. The mixing device 910 includes a swirl flow generating chamber for generating a swirl flow, a flow outlet through which a mixed chemical liquid flows out, and a narrowing chamber, which is provided between the swirl flow generating chamber and the flow outlet and which includes a space that continuously narrowed toward the flow outlet. When the ultrasonic motor 3 is rotated in reverse, the pressing unit 4 pulls back the piston 93 in a backward movement direction.

The syringe 91 filled with the chemical liquid may be a pre-filled syringe. The chemical liquid may be manually filled in the syringe 91, or may be filled in the syringe 91 by using the injecting apparatus 1 or a filling device. A data carrier, e.g., a radio-frequency identification (RFID) chip or a barcode, may be provided on the syringe 91. Information on the filled chemical liquid, for example, is recorded in the data carrier. The injecting apparatus 1 may be configured to control the injection pressure, for example, of the chemical liquid by reading the recorded information from the data carrier via the injection head 2. For example, the control device 5 may be configured to calculate an optimum injection amount for each weight based on the read information of the chemical liquid (iodine content, gadolinium content, etc.), and display the calculated optimum injection amount on the touch panel of the console 10.

When injecting the chemical liquid, the operator turns on the power supply of the injecting apparatus 1, and mounts the syringe 91. Then, the operator presses a start button 28 of the injection head 2. When an operation panel is provided on the injection head 2, the operator can also press an injection button on the operation panel. Further, the operator can also start the injection by pressing a button on the hand switch 14 or an injection button displayed on the touch panel. The operator may turn on the power supply of the injecting apparatus 1 after mounting the syringe 91.

The control device 5 is configured to transmit, when the injection button has been pressed, a normal-rotation signal as a drive voltage to the ultrasonic motor 3. When the shaft of the ultrasonic motor 3 normally rotates based on the normal-rotation signal, the encoder 39 detects the rotation and transmits a pulse signal to the control device 5. Then, when the syringe 91 is to be removed after the injection is finished, the control device 5 transmits a reverse-rotation signal as a drive voltage to the ultrasonic motor 3 in order to cause the piston 93 to move backward. The shaft of the ultrasonic motor 3 is rotated in reverse based on the reverse-rotation signal. The drive voltage transmitted to the ultrasonic motor 3 is an AC voltage. When a case where one of two types of drive voltages having different phases is delayed with respect to the other drive voltage is considered to be the normal-rotation signal, a case where the other drive voltage is delayed with respect to the one drive voltage is the reverse-rotation signal.

The control device 5 includes a memory unit 53 as a storage unit. The injection protocol is stored in the memory unit 53. The injection of the chemical liquid is automatically performed based on the injection protocol. The injection time, the injection rate, the injection amount, and an injection pressure limit value, for example, are set in the injection protocol. Because the content of the injection protocol is displayed on the console 10, the operator can verify the content of the injection protocol. The control device 5 is configured to control the injection time by using a timer (not shown), and to monitor the injection state, e.g., the injection pressure of the chemical liquid. Further, a storage medium on which the injection protocol is stored may be connected to the console 10, and the injection of the chemical liquid may be performed based on the injection protocol read from the storage medium. The injection protocol may be locked with a password so that the injection protocol cannot be changed.

The injection head 2 and the control device 5 are constructed from non-magnetic materials so that the injection head 2 and the control device 5 can be arranged in an examination room. Specifically, the injection head 2 and the control device 5 are constructed from materials such as stainless steel, aluminum, plastic, brass, copper, and ceramic. The console 10 arranged in the operation room may also be arranged in the examination room if the console 10 is constructed from non-magnetic materials. Further, the ultrasonic motor 3 is also constructed from non-magnetic materials. Specifically, the material for an elastic body is phosphor bronze, the material for the shaft, screws, and spacers is brass, the material for a case, a base, and a rotor is aluminum, and a material for the bushes is a fluororesin. As a result, the injecting apparatus 1 may be used near devices utilizing magnetism, e.g., an MRI apparatus. However, the injection head 2 and the control device 5 may be constructed from magnetic materials in the case that the injection head 2 and the control device 5 are to be used sufficiently away from the MRI apparatus, in the case that the injection head 2 and the control device 5 have been subjected to magnetic shielding treatment, or in the case that the injection head 2 and the control device 5 are to be used near another imaging apparatus.

As illustrated in FIG. 2, the console 10 is connected to the control device 5. A main central processing unit (CPU) 51 of the control device 5 is configured to transmit and receive signals to and from the console 10. The control unit 50 of the control device 5 is configured to control the ultrasonic motor 3. The power supply 55 is configured to supply power to the control unit 50 and the injection head 2. The main CPU (controller) 51 of the control unit 50, which is configured from a single-chip microcomputer, is configured to control the ultrasonic motor 3 and to execute processing operations, such as predetermined calculations, controls, and determinations, based on programs stored in advance in the memory unit 53. The memory unit 53 includes, for example, a random-access memory (RAM), which is a system work memory for operating the main CPU, a read-only memory (ROM) configured to store programs, system software, and the like, or a hard disk drive.

The main CPU 51 is configured to transmit and receive signals to and from a field-programmable gate array (FPGA) 56. The FPGA 56 is connected to a drive circuit (drive voltage generation unit) 52. The drive circuit 52 is connected to the ultrasonic motor 3. The encoder 39, which is configured to output a pulse signal corresponding to the rotational speed of the ultrasonic motor 3, is connected to the rotor of the ultrasonic motor 3. The encoder 39 is configured to output a pulse signal to the FPGA 56.

The main CPU 51, which has received a command signal for starting the injection, outputs a setting speed signal to the FPGA 56. The FPGA 56 is configured to generate, based on the setting speed signal, a sin generation signal, a −sin generation signal, a cos generation signal, and a −cos generation signal as drive signals for generating the drive voltage. The FPGA 56 is also configured to output the drive signals to the drive circuit 52. The drive circuit 52, which has received the drive signals, etc., generates an alternating current (AC) voltage (sin wave, cos wave) as the drive voltage for driving the ultrasonic motor 3, and outputs the generated AC voltage to the ultrasonic motor 3.

The injecting apparatus 1 may include a drive device in which the ultrasonic motor 3 and the control unit 50 are integrally arranged, and this drive device may drive the pressing unit 4. The control unit 50 may also be integrally arranged with the console 10.

[Adapter Detection Device]

The adapter 8, which is configured to mount the syringe 91 to the injection head 2, and which includes convex portions 83 (FIG. 4B), is attached to the syringe holder 92 illustrated in FIG. 1. The adapter detection units 6 (FIG. 5), which are configured to detect the adapter 8, are provided on the injection head 2 as adapter detection devices.

Figure 4A:
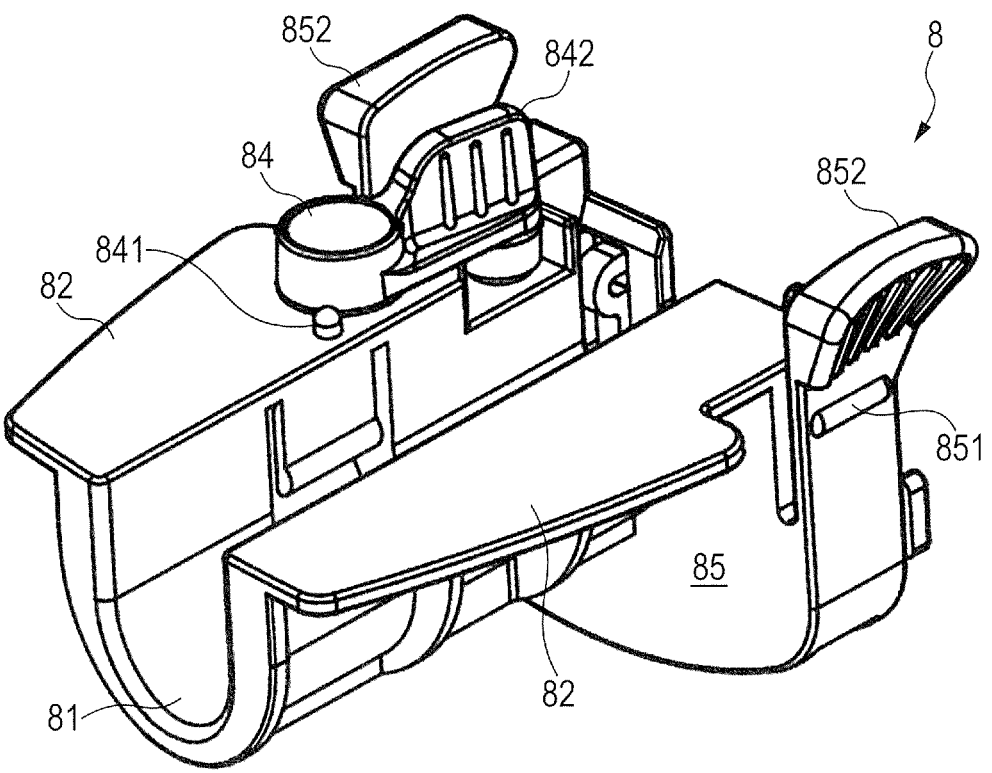
FIG. 4A is a schematic perspective view of an adapter as an example.
Figure 4B:
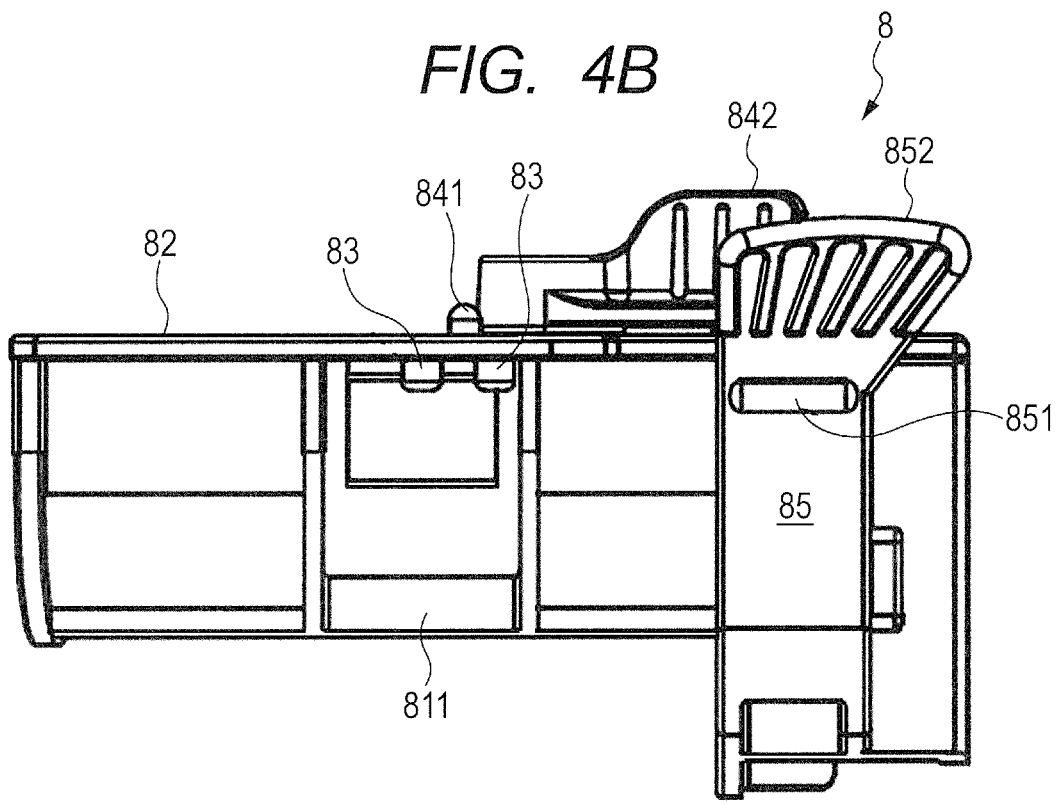
FIG. 4B is a schematic side view of the adapter as an example.
Figure 5:
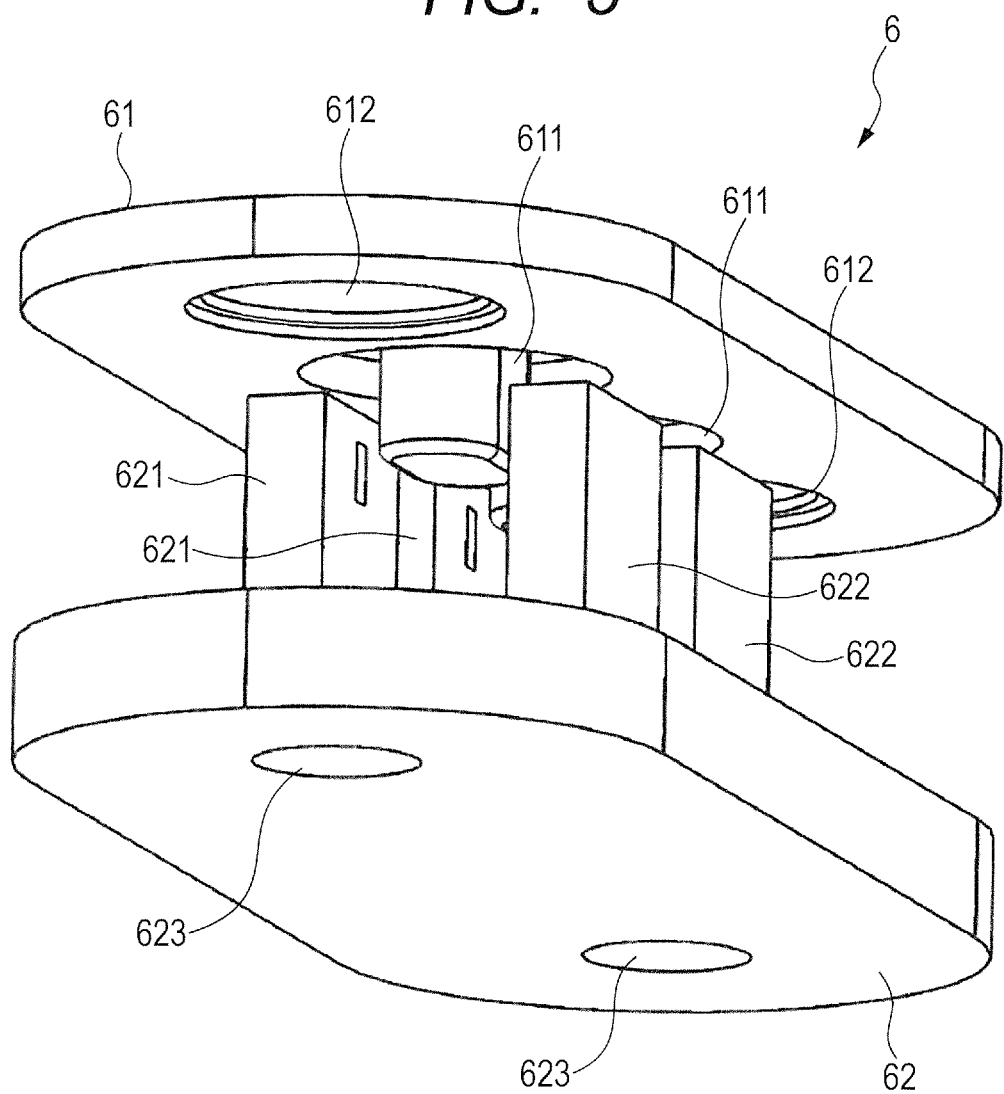
FIG. 5 is a schematic perspective view of an adapter detection device.
Figure 6:
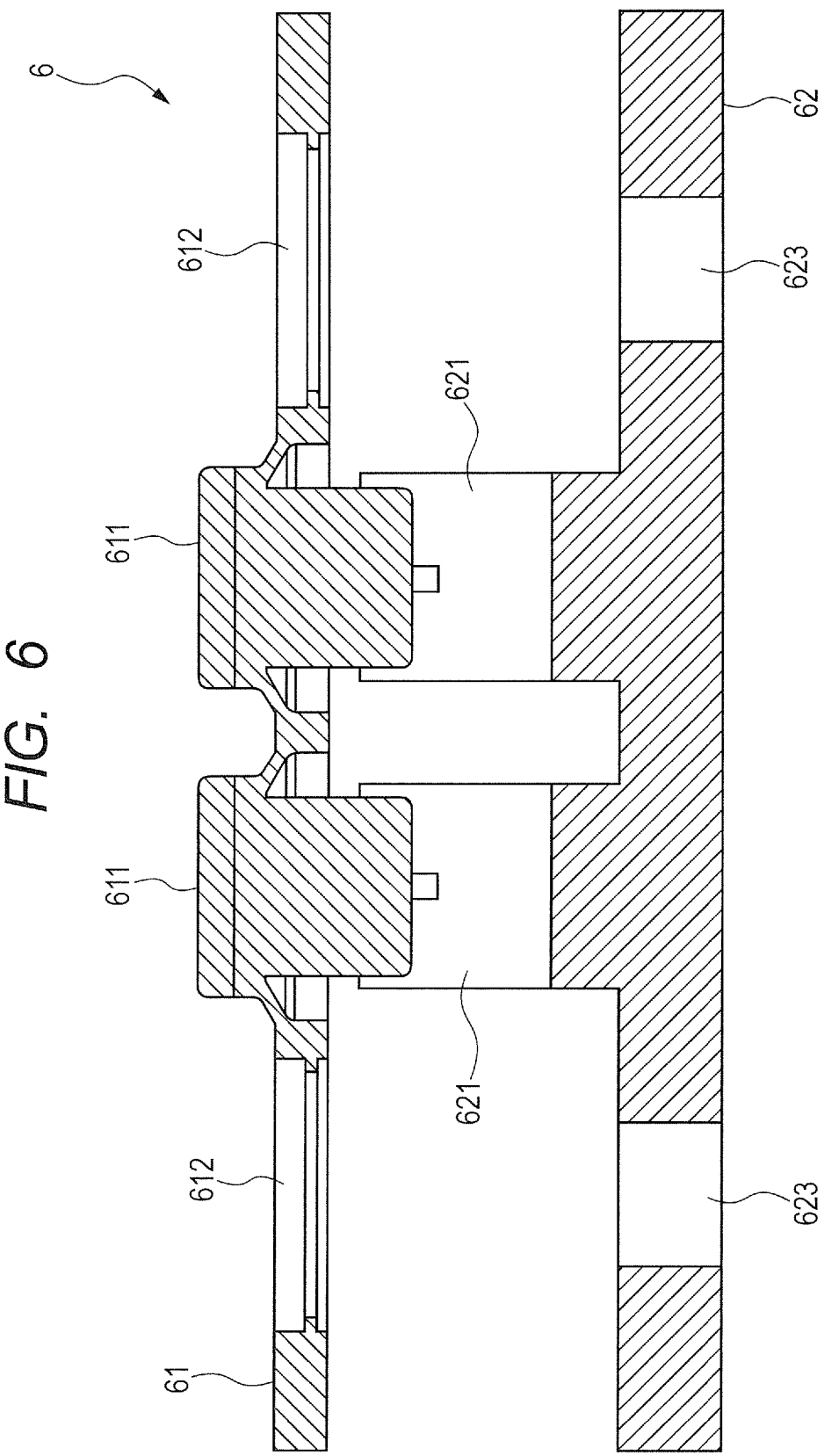
FIG. 6 is a schematic cross-sectional view of the adapter detection device.
Figure 7:
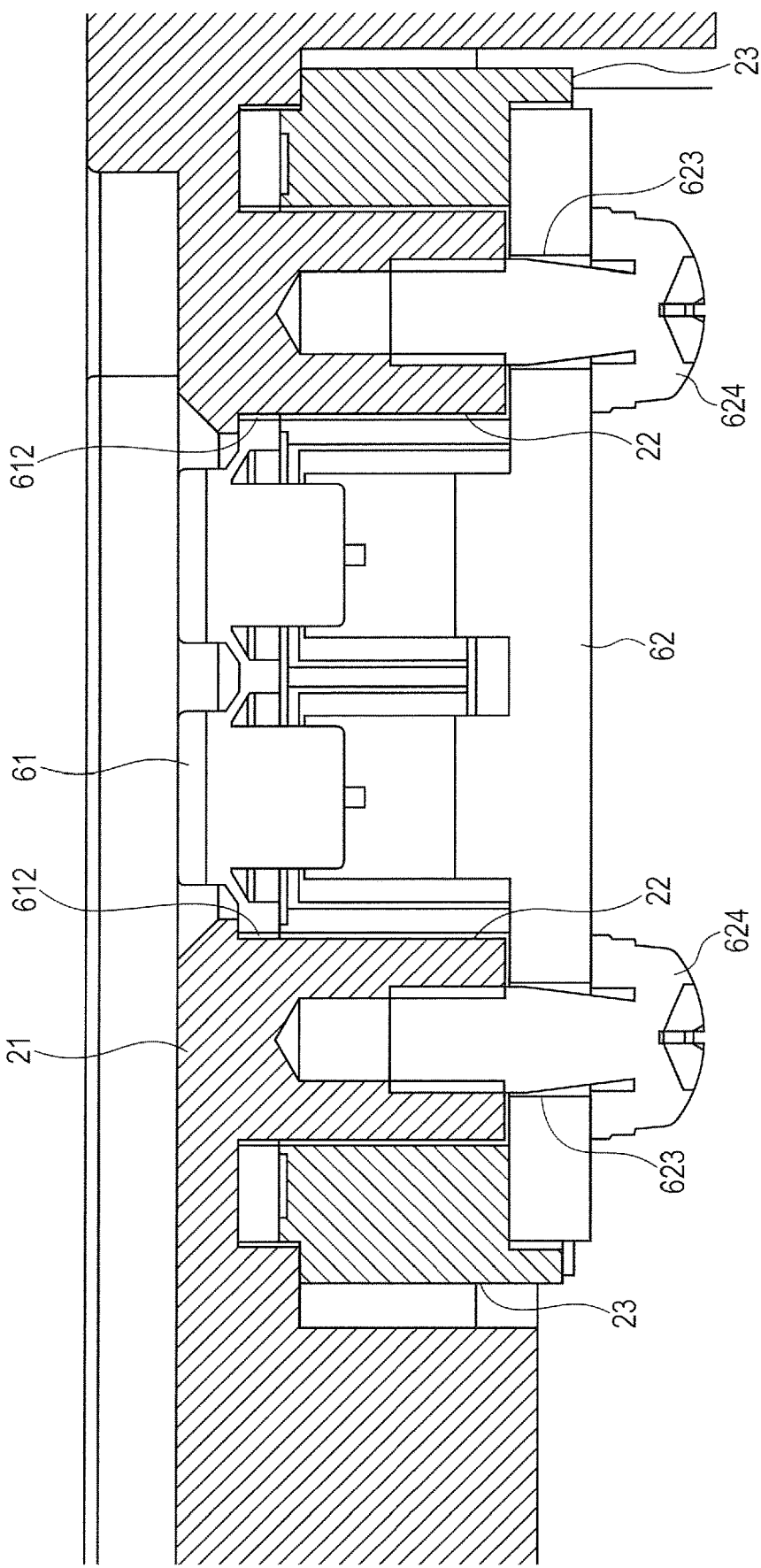
FIG. 7 is a schematic cross-sectional view for illustrating the fixed adapter detection device.

The adapter detection units 6 are now described with reference to FIG. 3 to FIG. 7. FIG. 3 is a schematic top view for illustrating a front end portion of the injection head 2 before the adapter 8 is attached. In FIG. 4A and FIG. 4B, an adapter 8 that can be attached to the syringe holder 92 on a contrast medium side is illustrated as an example of the adapter. FIG. 4A is a schematic perspective view for illustrating the adapter 8 as viewed from above. FIG. 4B is a schematic side view for illustrating the adapter 8 as viewed from an external perspective. FIG. 5 is a schematic perspective view for illustrating the adapter detection unit 6 as viewed from below. FIG. 6 is a schematic cross-sectional view taken along a longitudinal direction (forward/backward direction) of the adapter detection unit 6. FIG. 7 is a schematic cross-sectional view taken along the longitudinal direction of the fixed adapter detection unit 6.

As illustrated in FIG. 3, the adapter detection units 6 are provided at front-side, upper portions of the syringe holders 92. The adapter detection units 6 are configured to detect the adapters 8 attached to the syringe holders 92. A syringe 91 filled with a contrast medium is mounted to one of two syringe holders 92. Further, on that syringe holder 92, adapter detection units 6 are arranged on both sides of a concave portion into which the adapter 8 is to be inserted. A syringe 91 filled with a physiological saline is mounted to the other syringe holder 92. On that syringe holder 92, one adapter detection unit 6 is arranged on the side opposite to the contrast-medium-side syringe holder 92, namely, on the external side of the concave portion into which the adapter 8 is to be inserted.

Each adapter detection unit 6 includes a button 61 made from silicone rubber. The buttons 61 are pushed down by the convex portions 83 provided on the adapter 8. On the contrast-medium-side syringe holder 92, two buttons 61 are provided. On the physiological-saline-side syringe holder 92, one button 61 is provided.

At least one of the external shape or the material (e.g., glass or resin) of the syringe 91 may be different depending on the company that manufactured the syringe 91. There-fore, the adapter 8 is used in order to allow syringes 91 having a plurality of types of external shape to be mounted to the syringe holder 92. The adapter 8 is attached to the syringe holder 92, and the syringe 91 is mounted to the attached adapter 8. As a result, the syringe 91 is mounted to the injection head 2. Using different adapters 8 based on the external shape of the syringe 91 enables a plurality of types of syringe 91 to be mounted.

As illustrated in FIG. 4A, the adapter 8 includes a concave portion 81 on which the syringe 91 is to be mounted, flanges 82 extending toward an external side from the concave portion 81, and convex portions 83 provided on a lower side of the flanges 82. The concave portion 81 is curved in a substantially U-shape, and is inserted into a groove 921, which is curved in a substantially U-shape, of the syringe holder 92. Further, the concave portion 81 has an inner surface shape that is complementary to the outer shape of the syringe 91. As illustrated in FIG. 4B, a window 811 for externally observing the syringe 91 is formed in the concave portion 81. The convex portions 83 are provided on both of the flanges 82. However, the convex portions 83 may be provided on only one of the flanges 82.

The adapter 8 further includes a stopper arm as a holding member 84, which is provided on an upper surface of the flange 82 and which can freely rotate in a horizontal direction. The holding member 84 is capable of moving between a retracted position retracted from an upper opening of the concave portion 81 and a holding position protruding into the opening. The holding member 84 includes a lever 842. When the holding member 84 is rotated toward the holding position, the lever 842 abuts against a stopper 841, and the rotation is stopped. The holding member 84 positioned at the holding position abuts from above against an external surface of the syringe 91, which is positioned in the concave portion 81. As a result, the syringe 91 is firmly held from below by the concave portion 81 and from above by the holding member 84.

An elastic engagement unit 85 is provided at a rear portion of the adapter 8. An engaging groove 922, into which the engagement unit 85 is received, is provided in the syringe holder 92. The engaging groove 922 is in communication with the groove 921. Bump portions 851 are provided on an external surface of the engagement unit 85. Regulating portions 923 protruding inward are provided on an inner surface of the engaging groove 922. Grasping portions 852 are provided on an upper end of the engagement unit 85.

When the operator applies an inward-pressing force on the grasping portions 852, the shape of the engagement unit 85 changes such that both the grasping portions 852 come closer to each other. As a result, an external dimension of the engagement unit 85 changes, and hence the engagement unit 85 can be inserted into the engaging groove 922 such that the bump portions 851 pass over the regulating portions 923. When the operator subsequently releases the grasping portions 852, the engagement unit 85 returns to its original shape, and the bump portions 851 are positioned below the regulating portions 923. As a result, upward movement of the adapter 8 is regulated by the regulating portions 923. When the engagement unit 85 returns to its original shape, the external surface of the engagement unit 85 hits the engaging groove 922, causing a hitting sound to be produced. The operator can know that the adapter 8 has been correctly attached by recognizing the hitting sound.

As illustrated in FIG. 4B, the upper surfaces of the flanges 82 and an upper surface of the engagement unit 85 are formed flush with each other. A length from the upper surfaces of the flanges 82 to the lower edges of the convex portions 83 is shorter than a length from the upper surface of the engagement unit 85 to the lower edges of the bump portions 851. As a result, before the adapter 8 is attached, namely, before the bump portions 851 pass over the regulating portions 923, the convex portions 83 do not abut against the buttons 61 of the adapter detection units 6. This suppresses the adapter 8 from being erroneously detected before the adapter 8 is correctly attached.

The adapter 8 illustrated in FIG. 4A and FIG. 4B is an example, and an adapter 8 having another shape may also be attached to the injection head 2. For example, an adapter 8 including only any one of the holding member 84 and the grasping portions 852 may be attached to the injection head 2. Further, an adapter 8 that does not include the holding member 84 or the grasping portions 852 may be attached to the injection head 2.

As illustrated in FIG. 5 and FIG. 6, the adapter detection unit 6 includes the button 61, which is to be pushed down by the convex portions 83 of the adapter 8, and a sensor 62 configured to detect in a contactless manner the pushing down of the button 61. The sensor 62 is an optical slit sensor, which is arranged facing a plurality of the buttons 61 from below, and which is configured to detect in a contactless manner a button 61 that has been pushed down.

Specifically, each button 61 includes two abutment portions 611 configured to abut against the convex portions 83. When the abutment portions 611 are being pushed down by the convex portions 83, the shape of the abutment portions 611 changes so as to protrude downward. When the adapter 8 is removed and the convex portions 83 move away from the abutment portions 611, the abutment portions 611 return to their original shape due to the elastic force that the abutment portions 611 possess. The sensor 62 includes light emitting portions 621 and light receiving portions 622, which face each other. The sensor 62 is configured to detect the adapter 8 (pushing down of button 61) when light is blocked by the abutment portions 611. As a result, because the pushing down of the buttons 61 can be detected in a contactless manner, degradation over time due to contact between the buttons 61 and the sensor 62 can be prevented.

Each button 61 includes two hole portions 612 aligned in the longitudinal direction. The sensor 62 includes screw holes 623 facing the hole portions 612. As illustrated in FIG. 7, the buttons 61 are fixed to an inner side of a frame 21 of the injection head 2. Specifically, each button 61 fits into an inner side of the frame 21 by inserting fixing portions 22 protruding downward from the frame 21 into the hole portions 612. Restraining members 23 are arranged between the buttons 61 and the sensor 62. Then, the sensor 62 is fixed to the fixing portions 22 by screws 624 via the screw holes 623. The upper surfaces of the abutment portions 611 of the fixed buttons 61 are exposed to the outside via holes formed in the frame 21. In FIG. 7, the upper side corresponds to the external side of the frame 21.

The fixing of the buttons 61 from the inner side in the manner described above prevents the buttons 61 from becoming loose from the frame 21. Further, the buttons 61 are formed from a waterproof material. As a result, even when the chemical liquid leaks, infiltration of the chemical liquid into the frame 21 can be suppressed by the buttons 61.

[Adapter Detection]

Next, detection of the adapter 8 by the adapter detection unit 6 is described with reference to FIG. 2. An arrangement pattern of the convex portions 83 in the adapter 8 differs based on the mountable syringe type. For example, a syringe manufactured by company A may be mountable to an adapter having two convex portions 83 on each side (total of four convex portions 83), but a syringe manufactured by company B may not be mountable. On the other hand, a syringe manufactured by company B may be mountable to an adapter having one convex portion 83 on each side (total of two convex portions 83), but a syringe manufactured by company A may not be mountable. As a result, when the adapter 8 is detected, the type of the adapter 8 can be determined based on the arrangement pattern of the convex portions 83.

Specifically, the sensor 62 of the adapter detection unit 6 is configured to transmit, when an abutment portion 611 pushed down by a convex portion 83 is detected, a detection signal (ON signal) to the control unit 50. For example, the sensors 62 are configured to transmit to the control unit 50 detection signals indicating that two abutment portions 611 on each side have been detected. The control unit 50 is configured to store the arrangement pattern of the detected abutment portions 611 in the memory unit 53. The sensor 62 is also configured to transmit, when the adapter 8 has been removed and no abutment portions 611 are detected, a non-detection signal to the control unit 50.

The detection signal is transmitted to the main CPU 51 via the FPGA 56. A data table associating the arrangement patterns of the convex portions 83 and the types of the adapter 8 is stored in advance in at least one of the FPGA 56 or the memory unit 53 of the control unit 50. The control unit 50 is configured to refer to that data table, to determine the type of the adapter 8, and to temporarily store the determination result. As a result, the control unit 50 can acquire the type of the adapter 8 attached to the injection head 2.

The type of the adapter 8 corresponds to the syringe type. The syringe types corresponding to the types of the adapter 8 are stored in advance in at least one of the FPGA 56 or the memory unit 53. As a result, the control unit 50 can determine the syringe type. For example, the control unit 50 is configured to determine, when it is determined that the adapter 8 has two convex portions 83 on each side, that the mounted syringe type is a syringe manufactured by company A, and to temporarily store the determined type. The control unit 50 is also configured to simultaneously display the fact that the syringe is manufactured by company A as the syringe type on the console 10. A drug name may be displayed on the console 10 as the syringe type in place of, or in conjunction with, the manufacturing company.

Examples of the information stored in advance in association with the type of the adapter 8 include the manufacturing company, a forward movement distance when the rear end has been detected, an estimated distance to the rear end, a product name, the drug name, a product ID, a chemical classification, a contained component, a concentration, a viscosity, a syringe volume, a syringe pressure resistance, a cylinder inner diameter, a piston stroke, and the like. Storing those pieces of information in advance allows the control unit 50 to perform various determinations. For example, the control unit 50 may determine, when it is determined that the adapter 8 has two convex portions 83 on each side, the forward movement distance when the rear end has been detected.

The arrangement pattern of the convex portions 83 may be designed as appropriate. However, in the case of providing the convex portions 83 on only one side of the adapter 8, it is preferred to provide only one convex portion 83. When two convex portions 83 are provided on one side of the adapter 8 and the buttons 61 are pushed down, one side of the adapter 8 may be pushed up by the elastic force (restorative force) of the abutment portions 611. When one side of the adapter 8 is pushed up, the adapter 8 tilts, and thus the abutment portions 611 may be prevented from being correctly detected. For this reason, in the case that the convex portions 83 are provided on only one side, providing only one convex portion 83 enables the force received by the adapter 8 to be kept at a minimum, thereby enabling tilting to be suppressed. In particular, because the syringe 91 filled with the contrast medium is light, in the case of providing the convex portions 83 on only one side of the adapter 8 to which that syringe 91 is to be mounted, it is preferred that only one convex portion 83 be provided.

The control unit 50 is configured to reset, when the adapter 8 has been removed and the control unit 50 has received a non-detection signal from the adapter detection unit 6, the arrangement pattern temporarily stored in the memory unit 53, and to then prepare for the attaching of the next adapter 8. At this stage, the control unit 50 is configured to reset the arrangement pattern stored in the memory unit 53 when non-detection signals of all the abutment portions 611 have been received. For example, when an arrangement pattern including two abutment portions 611 on each side is stored, the control unit 50 does not reset the arrangement pattern until all four of the abutment portions 611 are no longer detected. This prevents the control unit 50 from performing a reset even when the attached adapter 8 has erroneously been tilted, and when a part of the abutment portions 611 is no longer detected. As a result, the control unit 50 is capable of suppressing an erroneous determination of the adapter 8 having been removed.

The number of abutment portions 611 of the button 61 is not limited to two. One abutment portion 611 or three or more abutment portions 611 may be provided. Further, one convex portion 83 or six or more convex portions 83 may be provided on the adapter 8 corresponding to the number of abutment portions 611. In addition, the number of buttons 61 is also not limited. One button 61 or three or more buttons 61 may be provided.

[Rear End Detection Device]

Figure 8:
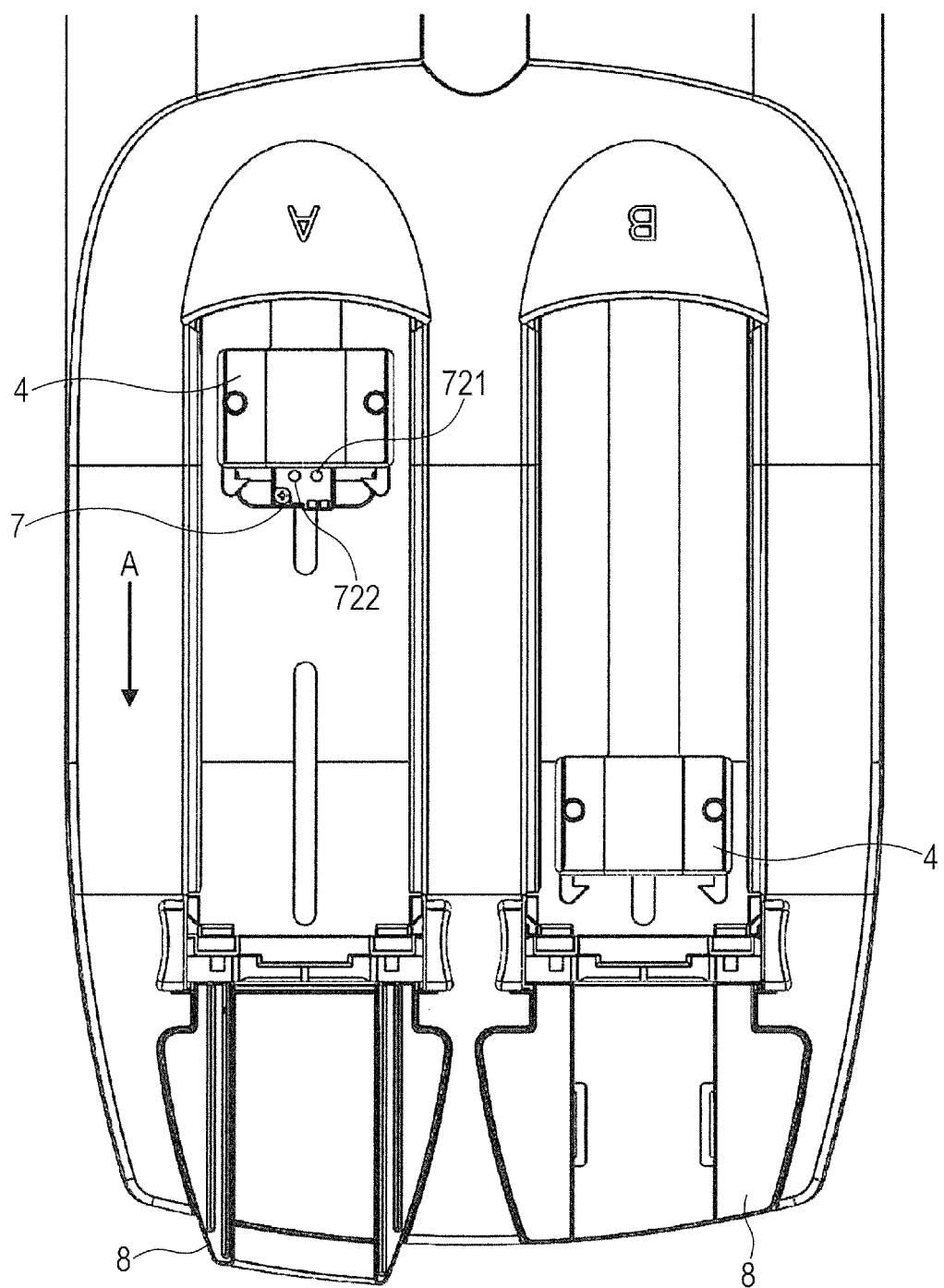
FIG. 8 is a schematic top view of a front-side portion of the injection head.
Figure 10A:
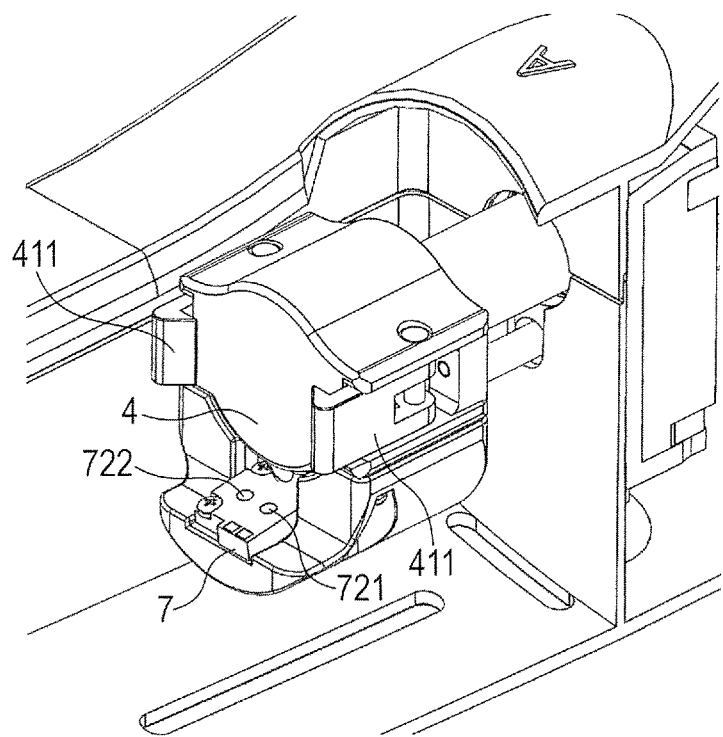
FIG. 10A is a schematic perspective view of a front end portion of a pushing unit.
Figure 10B:
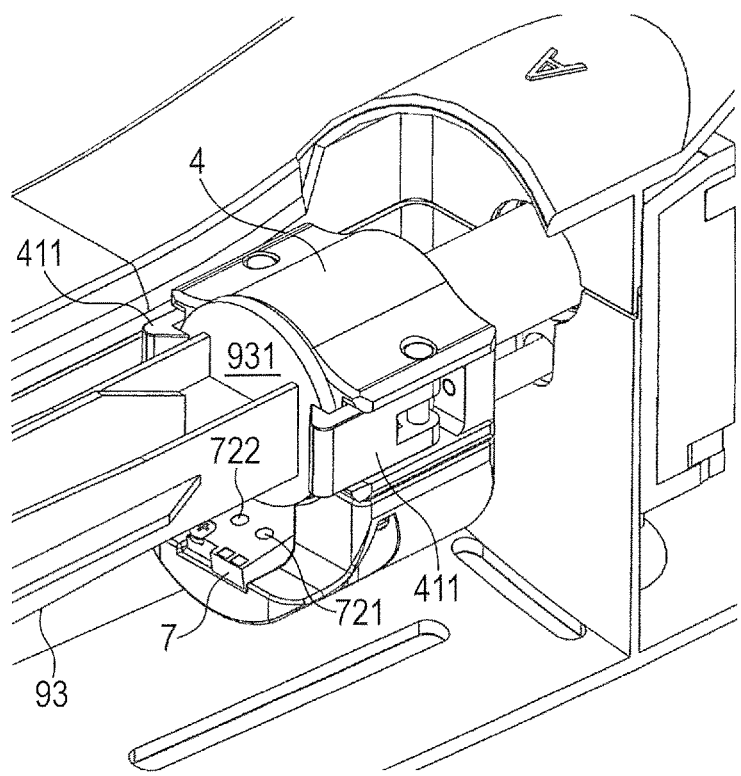
FIG. 10B is a schematic perspective view for illustrating how a rear end of a syringe is held.
Figure 11A:
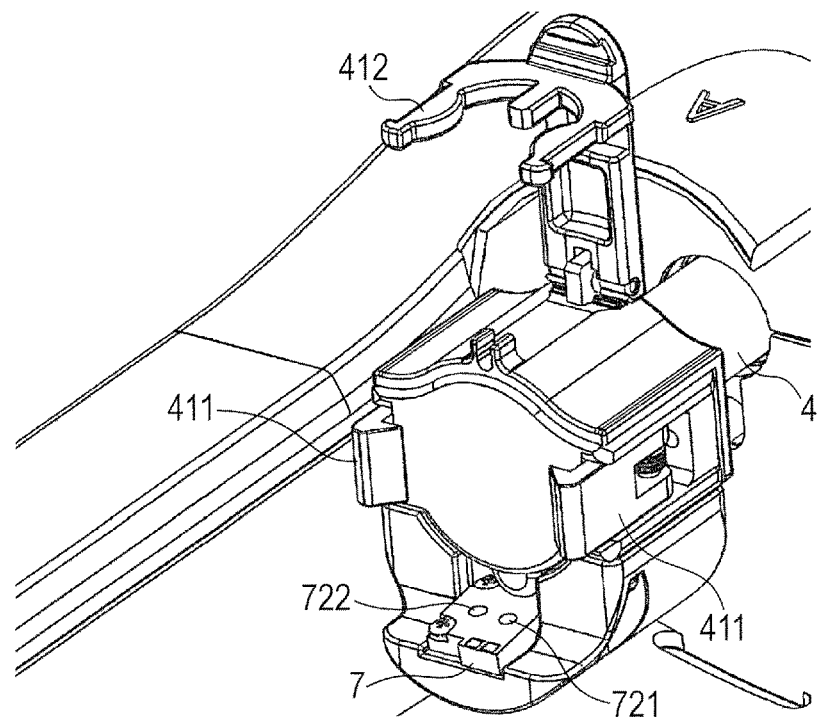
FIG. 11A is a schematic perspective view of the front end portion of the pushing unit.

The rear end detection unit 7 is provided on the injection head 2 as a rear end detection device configured to detect the rear end 931 of the syringe 91 in a contactless manner. The rear end detection unit 7 is now described with reference to FIG. 8 to FIG. 10. FIG. 8 is a schematic top view for illustrating a front-side portion of the injection head 2. The pushing unit 4 illustrated on the left side in FIG. 8 is at a completely moved-backward position, and the pushing unit 4 illustrated on the right side in FIG. 8 is at a completely moved-forward position. FIG. 9 is a schematic cross-sectional view taken along a longitudinal direction (forward/backward direction) of the rear end detection unit 7 and the piston 93. In FIG. 10A, a pushing unit 4 that is not holding the rear end 931 is illustrated, and in FIG. 10B, a pushing unit 4 that is holding the rear end 931 is illustrated. In FIG. 11A, a pushing unit 4 that is not holding the rear end 931 is illustrated, and in FIG. 11B, a pushing unit 4 that is holding the rear end 931 is illustrated.

As illustrated in FIG. 8 and FIG. 9, the rear end detection unit 7 is an optical sensor including a light emitting portion 721 and a light receiving portion 722. The pushing unit 4, which also functions as a holding unit configured to hold the rear end detection unit 7, is configured to hold the rear end detection unit 7. Specifically, the rear end detection unit 7 is held at a lower portion of the pushing unit 4 such that the light emitting portion 721 and the light receiving portion 722 protrude in front of the pushing unit 4. Visible light emitted from the light emitting portion 721 is reflected by the rear end 931 of the piston 93, and enters the light receiving portion 722. Light in other wavelengths, e.g., infrared light, may be used in place of visible light.

The light emitting portion 721 and the light receiving portion 722 are arranged side by side in a direction orthogonal to the forward movement direction of the pushing unit 4 indicated by the arrow A in FIG. 8. This allows reflected light to reliably enter the light receiving portion 722 even when the pushing unit 4 is moving forward. As a result, the rear end detection unit 7 can reliably detect the rear end 931.

As illustrated in FIG. 9, the rear end detection unit 7 is arranged to be tilted toward the syringe 91 side (tilted forward) with respect to a perpendicular line B of the abutment surface of the pushing unit 4. It is preferred that the tilt angle between an upper surface of the rear end detection unit 7 and the perpendicular line B be more than 0 degrees to 10 degrees or less. Arranging the rear end detection unit 7 in such a tilted manner enables reflected light from the abutment surface of the pushing unit 4 to be suppressed from entering the light receiving portion 722. As a result, erroneous detection of the rear end 931 by the rear end detection unit 7 can be suppressed. However, when reflected light from the abutment surface is not a problem, it is not necessary to arrange the rear end detection unit 7 in a tilted manner.

The rear end detection unit 7 is arranged on the pushing unit 4 on one of the two syringe holders 92 to which the syringe 91 filled with the contrast medium is mounted. However, the rear end detection unit 7 may also be arranged on the other pushing unit 4. The light emitting portion 721 is arranged on the other pushing unit 4 side with respect to the light receiving portion 722.

Holding of the rear end 931 by claws 411 is now described with reference to FIG. 10A and FIG. 10B. The pushing unit 4 includes the claws 411, which are configured to hold the rear end 931. The claws 411 are configured to, when the abutment surface of the pushing unit 4 approaches a rear surface of the rear end 931, be opened up and receive the rear end 931. The claws 411 are configured to then automatically move back to their original position due to a biasing force of a spring, and to hold the rear end 931 by engaging with edges on both sides of the rear end 931, as illustrated in FIG. 10B. When the pushing unit 4 moves forward in a held state, the piston 93 is pushed and inserted into a cylinder of the syringe 91, and the chemical liquid in the cylinder is extruded. On the other hand, when the pushing unit 4 moves backward, the piston 93 also moves backward, and if the chemical liquid container is connected to the syringe 91, the chemical liquid can be sucked into the cylinder. In this case, "approach" means, for example, that a distance between the abutment surface of the pushing unit 4 and the rear surface of the rear end 931 is less than 1 mm, and more preferred is a distance of less than 0.5 mm.

Figure 11B:
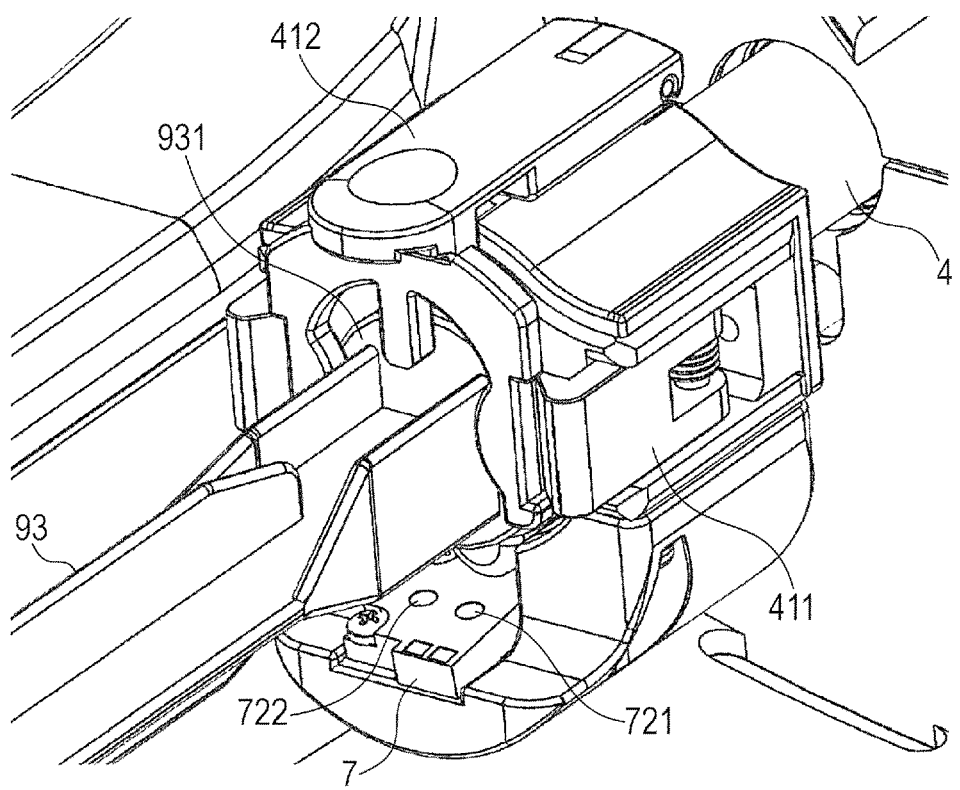
FIG. 11B is a schematic perspective view for illustrating how the rear end of the syringe is held.

Holding of the rear end 931 by a syringe hook 412 is now described with reference to FIG. 11A and FIG. 11B. The syringe hook 412, which is configured to hold the rear end 931, may be attached to the pushing unit 4. In the case that the syringe hook 412 is arranged, instead of the rear end 931 being held by the claws 411, the syringe 91 is held by the syringe hook 412. As a result, even when the syringe 91 has a small diameter that cannot be held by the claws 411, the syringe 91 may be moved forward or backward.

The syringe hook 412 is capable of being pivoted up and down. After the abutment surface of the pushing unit 4 has approached the rear surface of the rear end 931, the operator lowers the syringe hook 412 downward. As a result, as illustrated in FIG. 11B, because the rear end 931 is held from above, the rear end 931 is fixed to the pushing unit 4. When the pushing unit 4 moves forward in a held state, the piston 93 is pushed and inserted into the cylinder of the syringe 91, and the chemical liquid in the cylinder is extruded. On the other hand, when the pushing unit 4 moves backward, the piston 93 also moves backward, and if the chemical liquid container is connected to the syringe 91, the chemical liquid can be sucked into the cylinder.

[Stop-Assist Mode]

Figure 12:
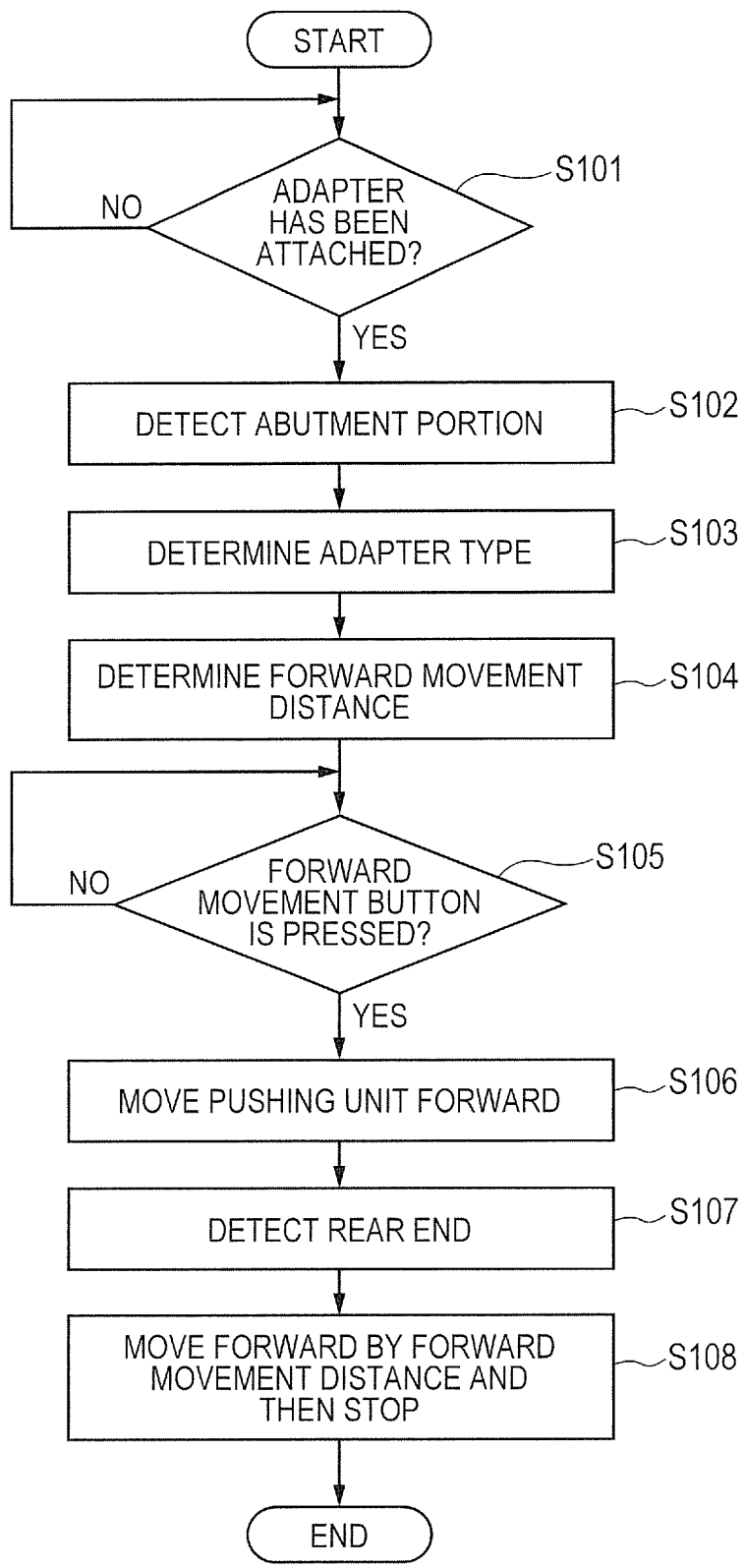
FIG. 12 is a flowchart for illustrating stopping of forward movement according to the first embodiment.

Next, stopping of forward movement in a stop-assist mode is described with reference to FIG. 12. In the stop-assist mode, the control unit 50 moves forward the pushing unit 4 by a predetermined forward movement distance after the rear end 931 has been detected, and stops the pushing unit 4 at a position separated from the rear end 931.

As described above, when the adapter 8 has been attached (YES in S101), the convex portions 83 push down the abutment portions 611. Then, the adapter detection unit 6 detects the pushed-down abutment portions 611 (S102), and transmits a detection signal to the control unit 50. When the adapter 8 has not been attached (NO in S101), Step S101 is repeated.

The control unit 50, which has received the detection signal, determines the arrangement pattern of the convex portions 83, and refers to a data table in which the arrangement pattern is associated with the type of the adapter 8. The control unit 50 then determines the type of the adapter 8 based on the arrangement pattern (S103). As a result, the control unit 50 can acquire the type of the adapter 8 attached to the injection head 2.

A data table associating the forward movement distance that the pushing unit 4 is to be moved forward after the rear end 931 has been detected (forward movement distance when rear end has been detected) and the type of the adapter 8 is stored in advance in at least one of the FPGA 56 or the memory unit 53. The control unit 50, which has acquired the type of the adapter 8, refers to that data table, and determines the corresponding forward movement distance based on the type of the adapter 8 (S104). As a result, the control unit 50 can acquire the forward movement distance when the rear end has been detected.

Because the pushing unit 4 is manually operated, during a period that the operator is pressing down a forward movement button 24 (FIG. 1) on the injection head 2 (YES in S105), the control unit 50 moves forward the pushing unit 4 (S106). When the operator is simultaneously pressing the forward movement button 24 and an acceleration button 25 (FIG. 1) on the injection head 2, the control unit 50 may accelerate the forward movement speed of the pushing unit 4. When the rear end detection unit 7 detects the rear end 931 of the piston 93 (S107), the rear end detection unit 7 transmits a detection signal to the control unit 50. When the forward movement button 24 is not being pressed (NO in S105), Step S105 is repeated.

Figure 13A:
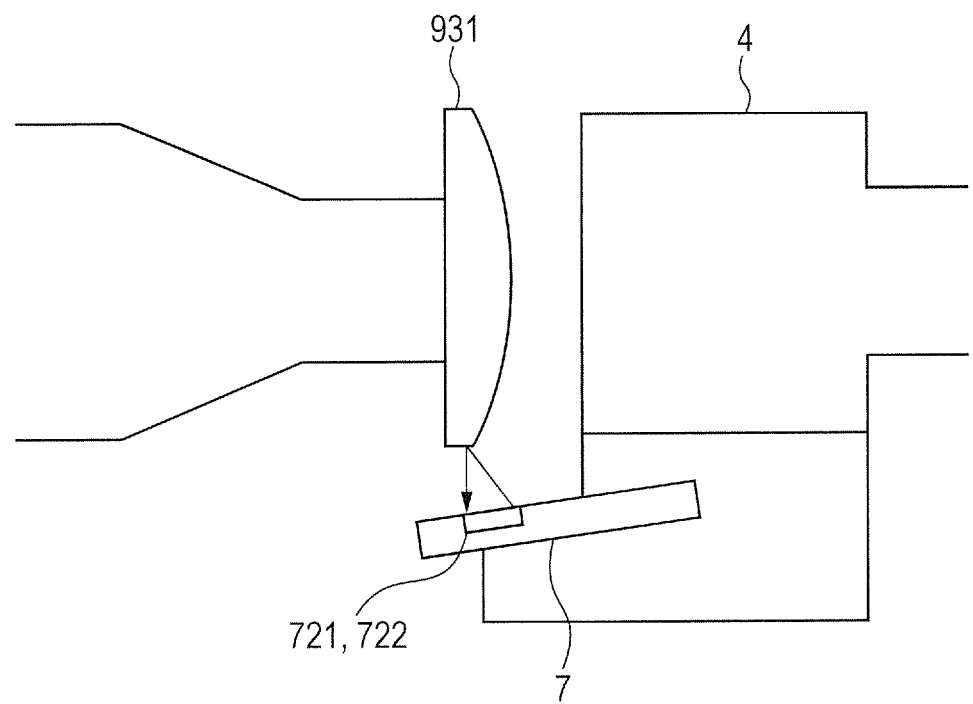
FIG. 13A is a schematic cross-sectional view for illustrating rear end detection.
Figure 13B:
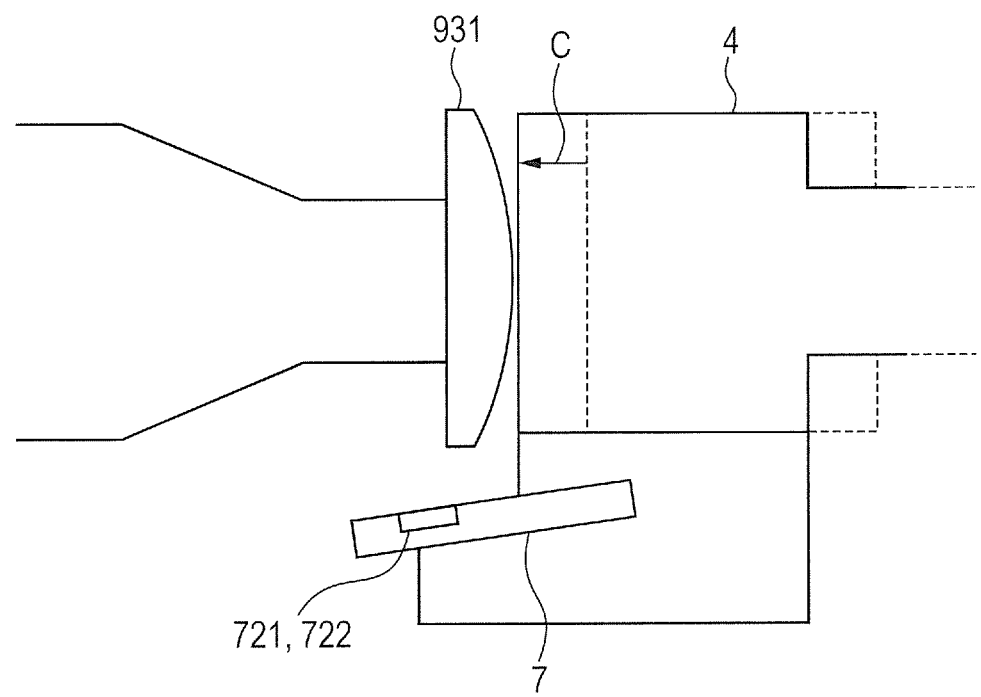
FIG. 13B is a schematic cross-sectional view for illustrating stopping of forward movement.

Stopping the forward movement after the rear end 931 has been detected is now described with reference to FIG. 13A and FIG. 13B. In FIG. 13A, a schematic cross-section of the rear end 931 and the pushing unit 4 when the rear end is detected is illustrated. In FIG. 13B, a schematic cross-section of the rear end 931 and the pushing unit 4 when forward movement is stopped is illustrated. To facilitate the description, the position of the pushing unit 4 when the rear end is detected is indicated in FIG. 13B by the dotted line.

As illustrated in FIG. 13A, the light emitting portion 721 and the light receiving portion 722 of the rear end detection unit 7 protrude in front of the pushing unit 4. As a result, light that has emitted from the light emitting portion 721 and been reflected by a lower side end surface of the rear end 931 enters the light receiving portion 722 before the pushing unit 4 abuts against the rear surface of the rear end 931. When the reflected light enters the light receiving portion 722, the rear end detection unit 7 transmits a detection signal to the control unit 50. At this stage, the abutment surface of the pushing unit 4 and the rear surface of the rear end 931 are separated.

As a result, when the rear end detection unit 7 detects the rear end 931 during the period that the forward movement button 24 is being pressed down, the control unit 50, which has received the detection signal, moves forward the pushing unit 4 by the forward movement distance acquired in advance (distance C in FIG. 13B), and then stops the pushing unit 4 at a position separated from the rear end 931 (S108). In other words, the control unit 50 stops the forward movement at a position at which the abutment surface of the pushing unit 4 does not abut against the rear surface of the rear end 931. As a result, the stop-assist mode is finished. In the stop-assist mode, the forward movement is stopped by the control unit 50 even when the forward movement button 24 is still being pressed down by the operator.

The forward movement distance is different depending on, for example, a shape, a thickness, a material, and a reflectance of the rear surface of the rear end 931. For example, the rear surface of the rear end 931 illustrated in FIG. 13A is curved. As a result, compared with when the rear surface is flat, the distance between the abutment surface of the pushing unit 4 and the rear surface of the rear end 931 when the rear end 931 is detected in FIG. 13A is shorter. Therefore, compared with when the rear surface is flat, the forward movement distance is set shorter. The control unit 50 is configured to determine the number of revolutions of the ultrasonic motor 3 based on a signal received from the encoder 39. The control unit 50 is also configured to determine the distance that the pushing unit 4 has been moved forward based on that number of revolutions. The control unit 50 may also be configured to determine the distance that the pushing unit 4 has been moved forward based on a time that the ultrasonic motor 3 is rotated normally at a predetermined speed.

After the pushing unit 4 has stopped, the operator again presses the forward movement button 24, and the abutment surface of the pushing unit 4 approaches the rear surface of the rear end 931. The rear end 931 is then held by the claws 411. Then, when injection preparation is complete, the operator presses a check button 27 (FIG. 1) on the injection head 2 or a check button on the console 10. As a result, the injection head 2 waits in a state ready to perform the injection.

The control unit 50 is configured to decrease a forward movement speed of the pushing unit 4 when the rear end detection unit 7 detects the rear end 931 during a period that the forward movement speed of the pushing unit 4 is being increased. In other words, the control unit 50, which has received a detection signal during a period that the operator is pressing the acceleration button 25, reduces the forward movement speed from an accelerated speed to a normal speed. As a result, the pushing unit 4 can be stopped more accurately at a desired position before the abutment surface of the pushing unit 4 abuts against the rear surface of the rear end 931. The control unit 50 may also be configured to further reduce the forward movement speed from the normal speed when the operator is not pressing the acceleration button 25, but the rear end detection unit 7 detects the rear end 931.

The control unit 50 is configured to move backward the pushing unit 4 during a period that the operator is pressing a backward movement button 26 (FIG. 1) on the injection head 2. The injecting apparatus 1 may be configured such that the pushing unit 4 is automatically moved backward to a predetermined position. For example, the injecting apparatus 1 may be configured such that, when the operator presses the backward movement button 26 on the injection head 2, the pushing unit 4 automatically moves backward to a position stored in advance.

[Modified Example]

A spacer may be attached to the rear end 931 so as to be positioned between the pushing unit 4 and the rear end 931. In this case, the rear end detection unit 7 is configured to detect the rear end of the spacer as the rear end 931 of the syringe 91. The injecting apparatus 1 may also be configured such that the pushing unit 4 automatically moves forward. For example, the injecting apparatus 1 may be configured such that when the operator presses the forward movement button 24 on the injection head 2, the pushing unit 4 automatically moves forward until the rear end detection unit 7 detects the rear end 931.

With the injecting apparatus 1 according to the first embodiment described above, the adapter detection unit 6 is configured to detect in a contactless manner a button 61 that has been pushed down. As a result, because the pushing down of the button 61 can be detected in a contactless manner, degradation over time due to contact between the buttons 61 and the sensor 62 can be prevented.

The control unit 50 is configured to acquire in advance the forward movement distance in accordance with the syringe 91 to be mounted, and after the rear end detection unit 7 detects the rear end 931, to stop the pushing unit 4 at the position to which the pushing unit 4 has moved by that forward movement distance. This enables the pushing unit 4 to be stopped so that the abutment surface of the pushing unit 4 does not abut against the rear surface of the rear end 931. As a result, the forward movement of the pushing unit 4 can be stopped just before the pushing unit 4 abuts against the rear end 931 of the piston 93. This also enables unwanted extrusion of the chemical liquid from the syringe 91 to be reliably prevented.

The control unit 50 is configured to stop the pushing unit 4 after the rear end detection unit 7 detects the rear end 931. As a result, even when the piston 93 is positioned further forward than an unused position due to a small amount of the chemical liquid having been injected in order to let out air, the pushing unit 4 can be caused to approach the rear end 931 and then be stopped. In the case that a foreign object, e.g., a finger, is present between the pushing unit 4 and the rear end 931, when the rear end detection unit 7 detects the foreign object, the forward movement of the pushing unit 4 is stopped. As a result, fingers, etc. can be prevented from being erroneously clamped.

Second Embodiment

Figure 14:
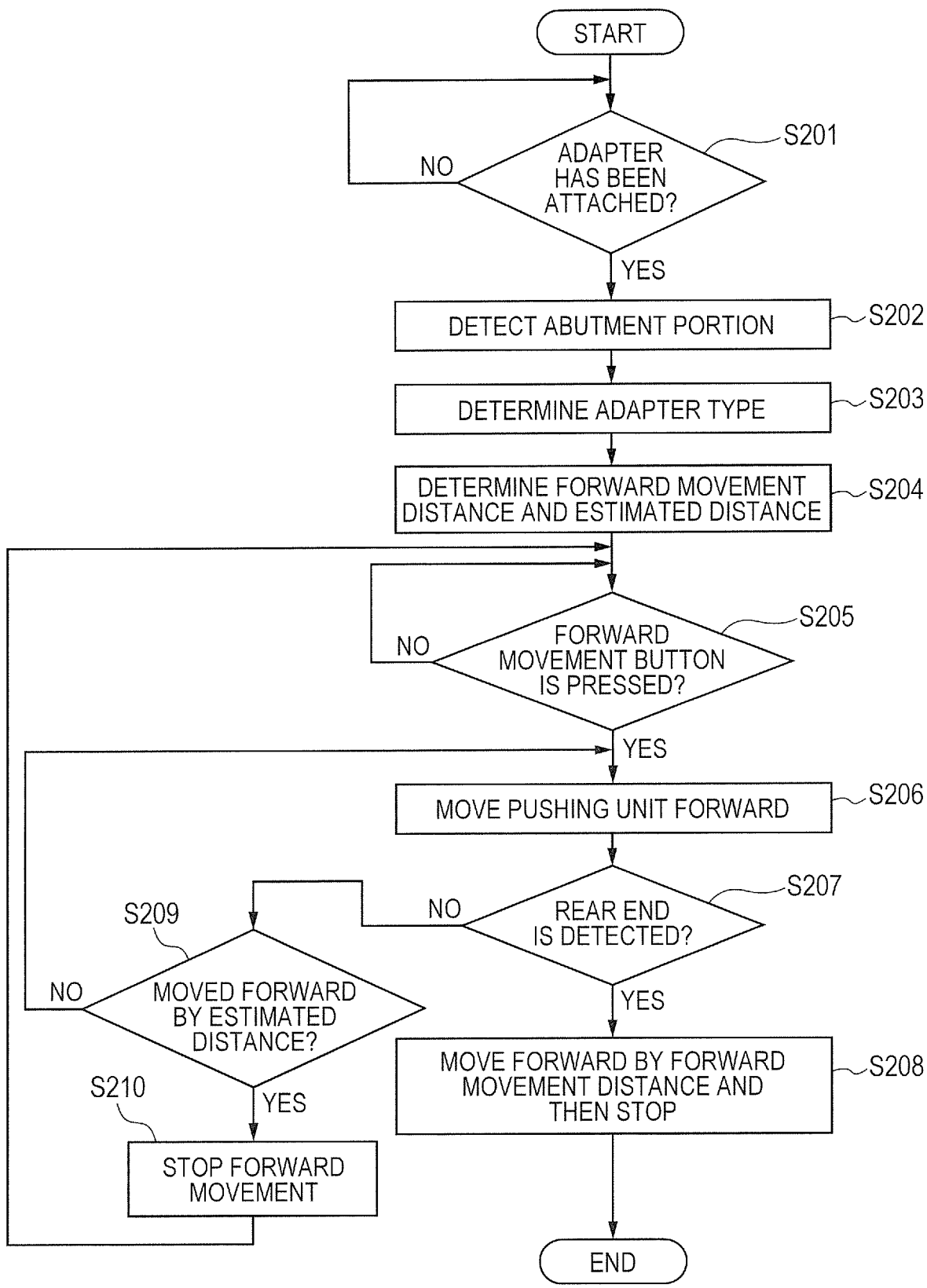
FIG. 14 is a flowchart for illustrating stopping of forward movement according to a second embodiment of the present invention.

An injecting apparatus 1 according to a second embodiment of the present invention is now described with reference to FIG. 14. The injecting apparatus 1 according to the second embodiment includes a temporary stop mode. In the temporary stop mode, the control unit 50 acquires an estimated distance that the pushing unit 4 is to be moved forward, and stops, in a case that the pushing unit 4 has been moved forward by the estimated distance before the rear end 931 is detected, even when the pushing unit 4 and the rear end 931 has not been detected. In the description of the second embodiment, differences from the first embodiment are described. Components that have been described in the first embodiment are denoted by the same reference numerals, and a description thereof is omitted. Unless described otherwise, components denoted with the same reference numerals have substantially the same operation and function, and their action and effect is substantially the same action and effect.

In the second embodiment as well, when the adapter 8 has been attached (YES in S201), the adapter detection unit 6 detects the pushed-down abutment portions 611 (S202), and transmits a detection signal to the control unit 50. The control unit 50 then refers to the data table, and determines the type of the adapter 8 based on the arrangement pattern of the abutment portions 611 (S203). The control unit 50, which has acquired the type of the adapter 8, then refers to the data table, and determines the forward movement distance corresponding to the type of the adapter 8 (S204).

In the second embodiment, a data table associating the type of the adapter 8 and the estimated distance, which corresponds to the distance that the pushing unit 4 is to be moved forward until the rear end detection unit 7 detects the rear end 931 of an unused syringe 91, is stored in advance in at least one of the FPGA 56 or the memory unit 53. The control unit 50, which has acquired the type of the adapter 8, refers to that data table, and determines the estimated distance corresponding to the type of the adapter 8 (S204).

When the operator is pressing the forward movement button 24 on the injection head 2 (YES in S205), the control unit 50 moves forward the pushing unit 4 (S206). During the forward movement, the control unit 50 stores in the memory unit 53 the distance that the pushing unit 4 has actually moved forward, and compares the acquired estimated distance and the actually moved forward distance. Even when the rear end detection unit 7 has not detected the rear end 931 (NO in S207), in a case that it is determined by the control unit 50 that the pushing unit 4 has been moved forward by the estimated distance (YES in S209), the control unit 50 stops the forward movement (S210).

Then, the injecting apparatus 1 waits until the forward movement button 24 is pressed down. When the operator again presses the forward movement button 24 (YES in S205), the control unit 50 again moves forward the pushing unit 4 (S206). Then, when the rear end detection unit 7 detects the rear end 931 of the piston 93 (YES in S207), the rear end detection unit 7 transmits a detection signal to the control unit 50. The control unit 50, which has received the detection signal, stops the forward movement of the pushing unit 4 after the pushing unit 4 has been moved forward by the forward movement distance (S208). When it is determined by the control unit 50 that the pushing unit 4 has not been moved forward by the estimated distance (NO in S209), the control unit 50 continues the forward movement (S206).

After the pushing unit 4 has stopped, the operator presses the forward movement button 24, and the abutment surface of the pushing unit 4 approaches the rear surface of the rear end 931. The rear end 931 is then held by the claws 411. Then, when injection preparation is complete, the operator presses the check button 27 (FIG. 1) on the injection head 2. As a result, the injection head 2 waits in a state ready to perform the injection.

During the period that the operator is pressing the acceleration button 25, when it is determined by the control unit 50 that the pushing unit 4 has been moved forward by the estimated distance, the forward movement speed is reduced from the accelerated speed to the normal speed. As a result, the pushing unit 4 can be stopped more reliably before the abutment surface of the pushing unit 4 abuts against the rear surface of the rear end 931. After the forward movement speed has been reduced to the normal speed, the operator can release the temporary stop mode by again pressing the acceleration button 25. In this case, the control unit 50 moves forward the pushing unit 4 until the rear end detection unit 7 detects the rear end 931. The control unit 50 may also be configured such that the temporary stop mode is selectable by the operator.

With the injecting apparatus 1 according to the second embodiment described above, the control unit 50 is configured to stop the forward movement even when the rear end detection unit 7 cannot detect the rear end 931 due to such a reason that, for example, the light emitting portion 721 or the light receiving portion 722 is dirty. This enables the pushing unit 4 to be stopped such that the abutment surface of the pushing unit 4 does not abut against the rear surface of the rear end 931 even when detection is not possible. As a result, the forward movement of the pushing unit 4 can be stopped just before the pushing unit 4 abuts against the rear end 931 of the piston 93. This also enables unwanted extrusion of the chemical liquid from the syringe 91 to be reliably prevented.

Third Embodiment

Next, an injecting apparatus 1 according to a third embodiment of the present invention is described. In the third embodiment, syringes 91 in a plurality of sizes may be mounted to one adapter 8. For example, there are cases in which a plurality of sizes, such as a 10 ml size, a 15 ml size, and a 20 ml size, are mounted to the adapter 8 illustrated in FIG. 4A and FIG. 4B. For a 20 ml size syringe 91, the position of the rear end 931 may be positioned further to the rear than for a 10 ml size syringe 91. In other words, the positions of the rear ends 931 of the syringes 91 mounted to one adapter 8 may be different. In such a case, the control unit 50 of the third embodiment is configured to acquire the forward movement distance based on the type of the adapter 8 and the distance that the pushing unit 4 is to be moved forward until the rear end detection unit 7 detects the rear end 931.

In the description of the third embodiment, differences from the first and second embodiments are described. Components that have been described in the first and second embodiments are denoted by the same reference numerals, and a description thereof is omitted. Unless described otherwise, components denoted with the same reference numerals have substantially the same operation and function, and their action and effect is substantially the same action and effect.

In the third embodiment as well, when the adapter 8 has been attached, the adapter detection unit 6 detects the pushed-down abutment portions 611, and transmits a detection signal to the control unit 50. The control unit 50 then refers to the data table, and determines the type of the adapter 8 based on the arrangement pattern.

In the third embodiment, the control unit 50, which has acquired the type of the adapter 8, refers to the data table, and determines a plurality of forward movement distances corresponding to one type of adapter 8 and a plurality of estimated distances corresponding to that one type of adapter 8. For example, the control unit 50 determines the forward movement distances for the syringes 91 having a 10 ml size, a 15 ml size, and a 20 ml size, and the estimated distances corresponding to those syringes 91. Then, the injecting apparatus 1 waits until the forward movement button 24 is pressed down. The control unit 50 moves forward the pushing unit 4 when the operator is pressing the forward movement button 24 of the injection head 2.

The control unit 50 stores in the memory unit 53 the distance that the pushing unit 4 actually moved forward until the rear end detection unit 7 detects the rear end 931. The control unit 50 then compares, when the rear end detection unit 7 detects the rear end 931, the acquired estimated distance and the actually moved forward distance. The control unit 50 determines an estimated distance that approximates the actually moved forward distance, and determines a forward movement distance corresponding to that estimated distance. The control unit 50 also stops the forward movement when the pushing unit 4 has been moved forward by the acquired forward movement distance.

After the pushing unit 4 has stopped, the operator presses the forward movement button 24, and the abutment surface of the pushing unit 4 approaches the rear surface of the rear end 931. The rear end 931 is then held by the claws 411. Then, when injection preparation is complete, the operator presses the check button 27 (FIG. 1) on the injection head 2. As a result, the injection head 2 waits in a state ready to perform the injection.

The control unit 50, which has determined the forward movement distance corresponding to the estimated distance, may also determine the syringe type corresponding to the forward movement distance. In this case, the control unit 50 is configured to display the determined syringe type on the console 10. The control unit 50 may also determine, based on an estimated distance approximating the actually moved forward distance, the syringe type corresponding to that estimated distance.

With the injecting apparatus 1 according to the third embodiment described above, even when syringes 91 in a plurality of sizes are mountable to one adapter 8, the forward movement distance in accordance with the size can be determined.

In the third embodiment as well, the pushing unit 4 may be stopped such that the abutment surface of the pushing unit 4 does not abut against the rear surface of the rear end 931. As a result, the forward movement of the pushing unit can be stopped just before the pushing unit abuts against the end of the piston. This also enables unwanted extrusion of the chemical liquid from the syringe to be reliably prevented.

A data table associating a volume (size) of the syringe 91 and the estimated distance may be stored in advance. When the operator selects the volume, the control unit 50 may determine the estimated distance corresponding to the selected volume by referring to that data table.

[Screen Configurations]

Figure 15:
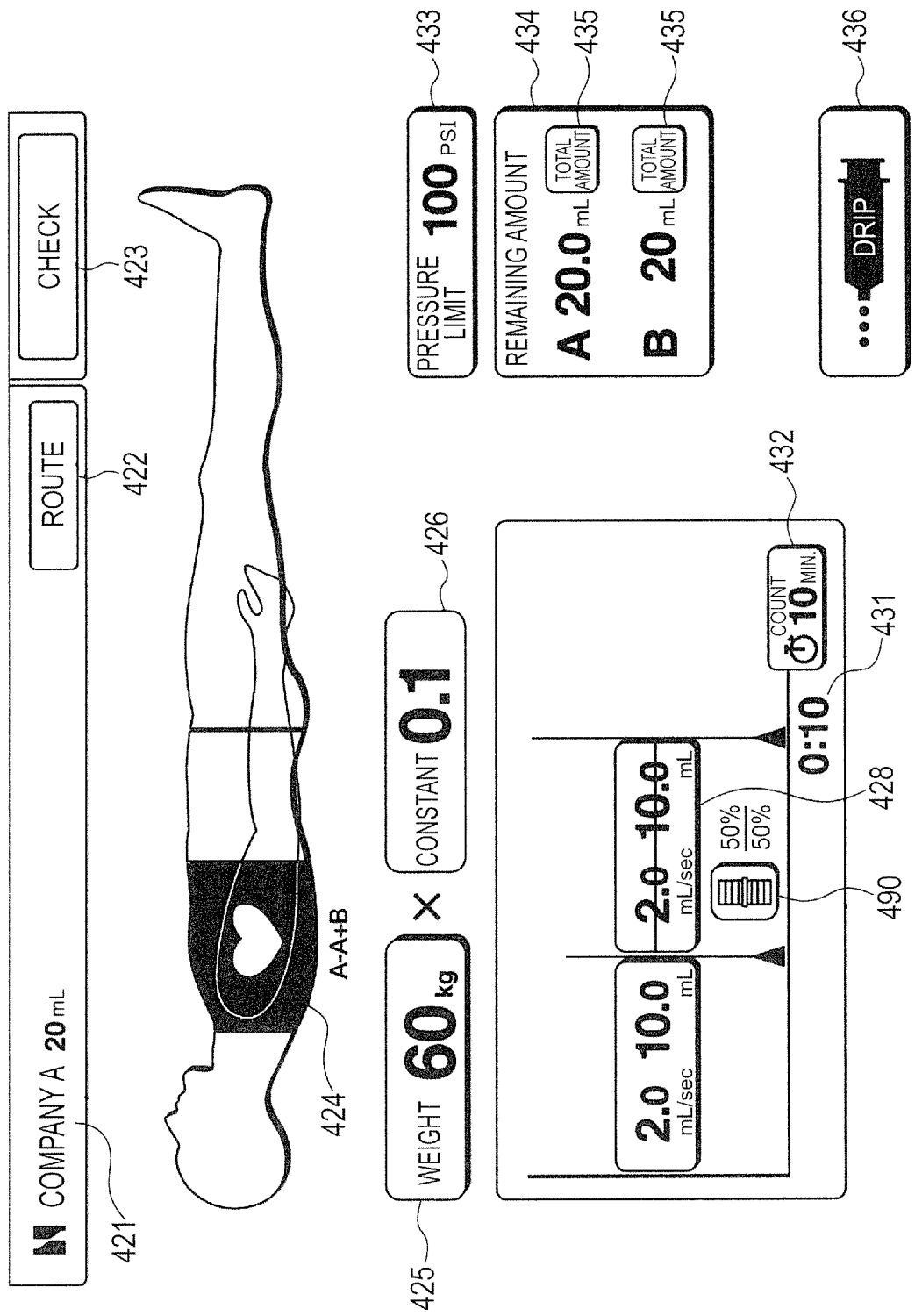
FIG. 15 is a schematic diagram for illustrating an input screen of an injection condition.
Figure 16:
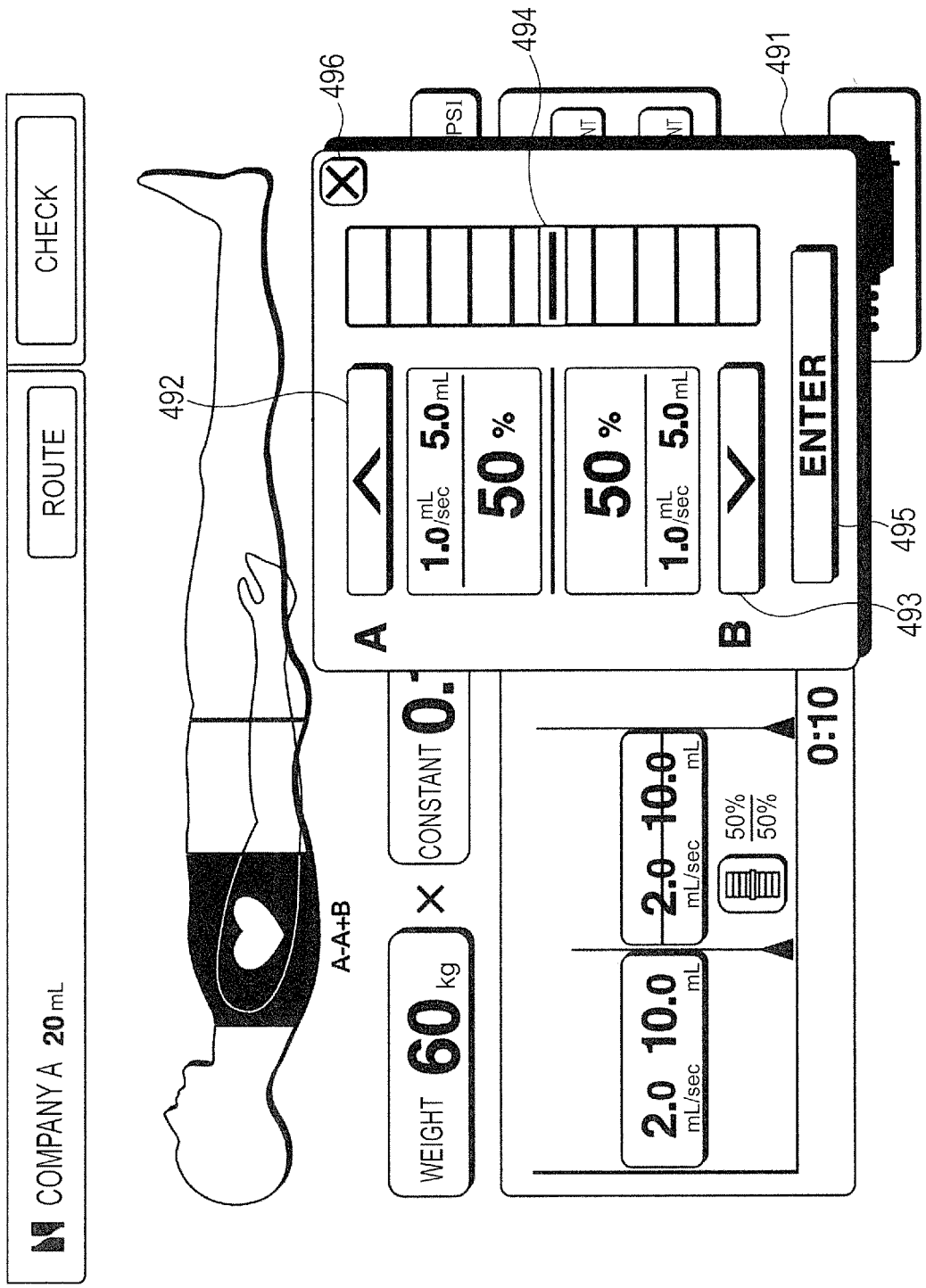
FIG. 16 is a schematic diagram for illustrating an adjustment screen of a mixing ratio.
Figure 17:
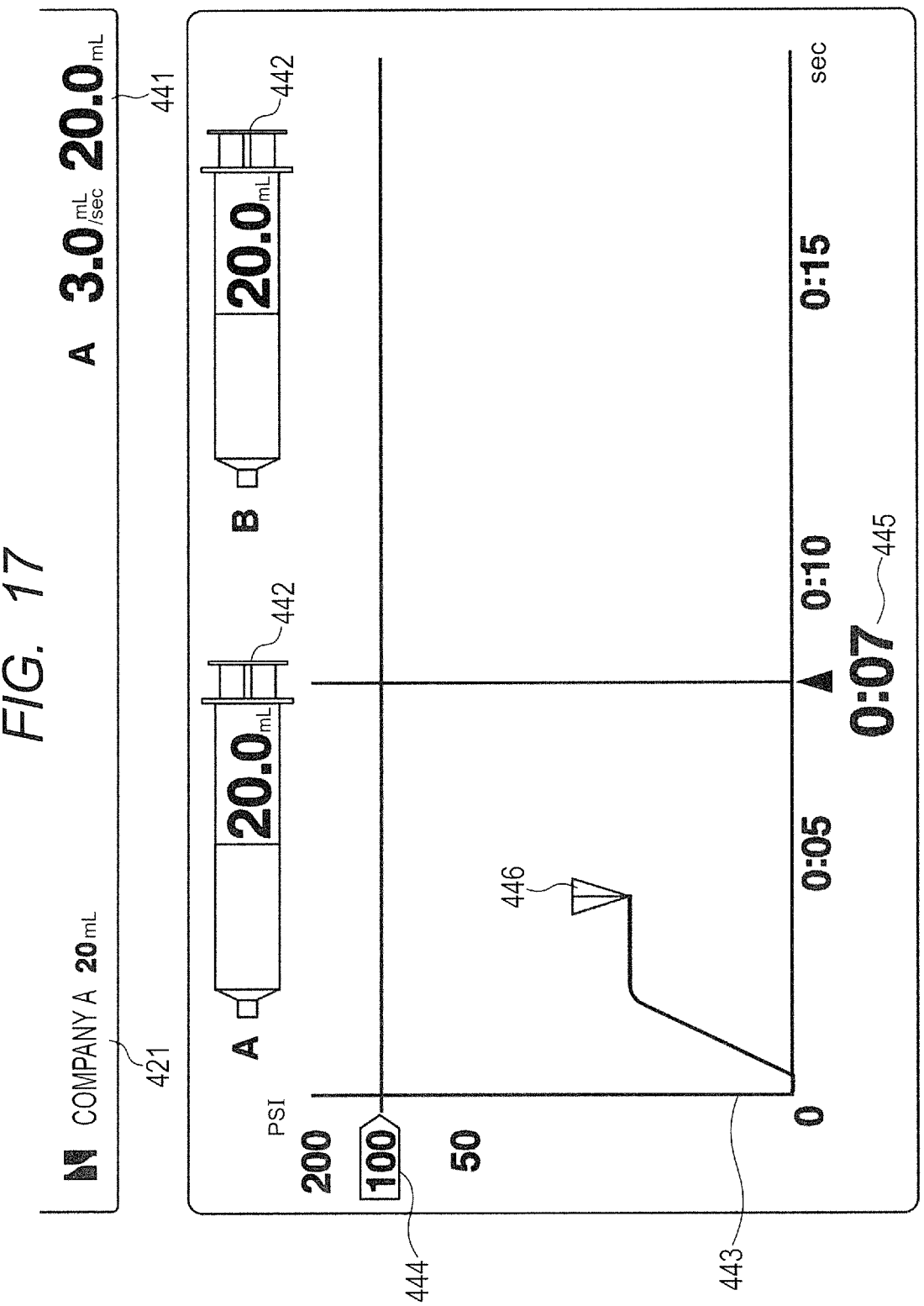
FIG. 17 is a schematic diagram for illustrating an injection screen.
Figure 18:
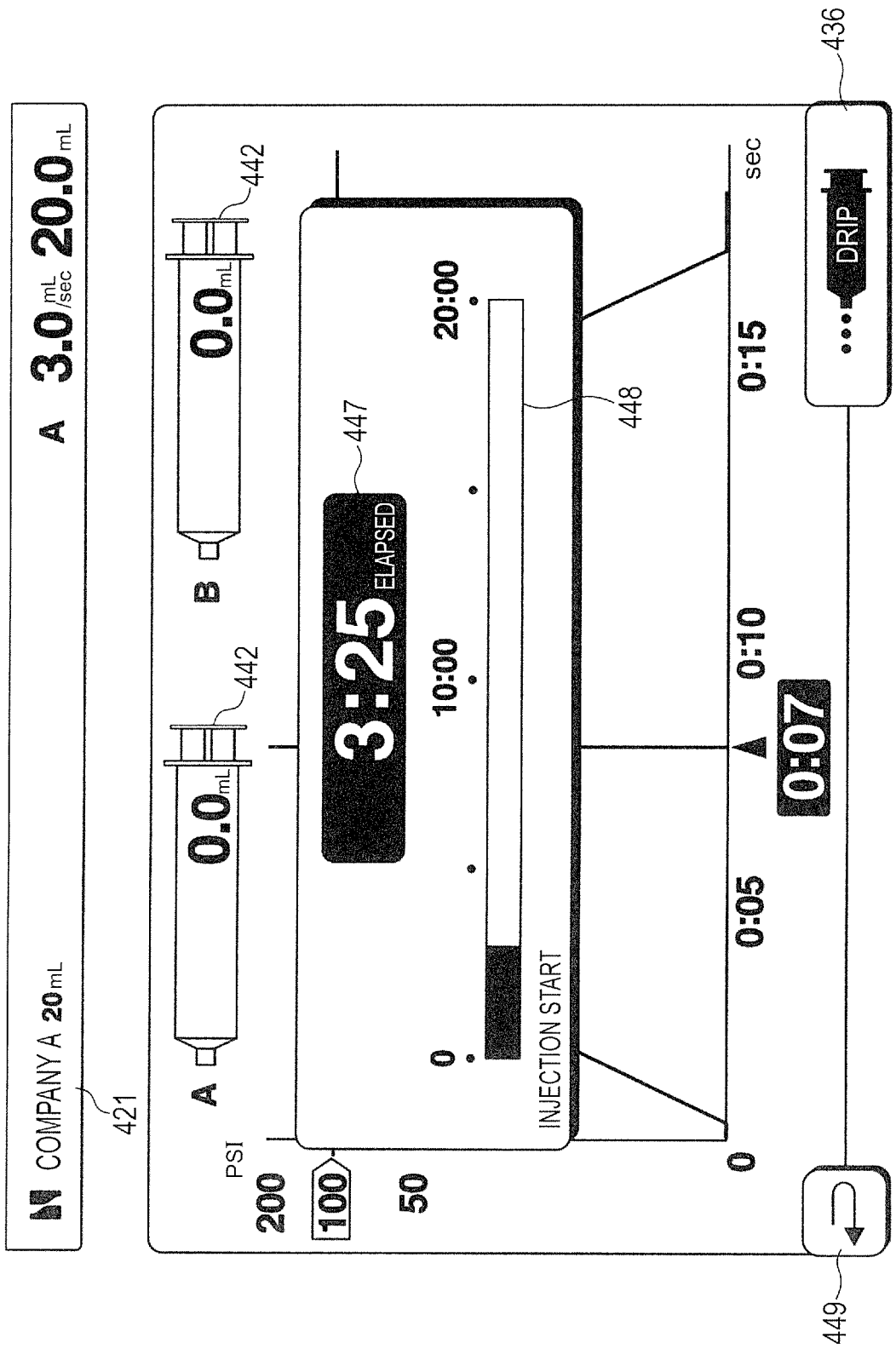
FIG. 18 is a schematic diagram for illustrating an elapsed time screen.

Next, the screens to be displayed on the console 10 of the injecting apparatus 1 according to each of the embodiments described above are described with reference to FIG. 15 to FIG. 18. In FIG. 15, an input screen of an injection condition is schematically illustrated. In FIG. 16, an adjustment screen of a mixing ratio is schematically illustrated. In FIG. 17, an injection screen is schematically illustrated. In FIG. 18, an elapsed time screen is schematically illustrated.

On the input screen of an injection condition illustrated in FIG. 15, syringe information 421, such as the syringe type (e.g., company name or syringe size), determined by the control unit 50 is displayed on an upper portion of the screen. When syringes 91 in a plurality of sizes are mountable to one adapter 8 as in the third embodiment, a plurality of syringe types are displayed. In the case that the control unit 50 has determined the syringe type, the determined syringe type is highlighted. In the case that the operator has input the syringe type, the input syringe type is highlighted.

Examples of the highlighting of the syringe type include displaying in a different color from that of the other indications, displaying in a larger size than the other indications, displaying the other indications in a smaller size, and not displaying the other indications. When the syringe 91 is not mounted, or when a non-supported syringe 91 is mounted, a "Non select" indication is displayed in the syringe information 421.

When the operator selects a route key 422, a route verification screen is displayed. In a status indication 423, as a status of the injecting apparatus 1, "Check", which indicates that injection preparation is not complete, or "Start OK", which indicates that the check button 27 has been pressed and the injection can be performed, is displayed. In a site and site details indication 424, a selected examination site or detailed site name is highlighted. In a weight key 425, a set weight is displayed. When the operator selects the weight key 425, an input screen is displayed. The weight can be set from that input screen.

In a constant key 426, a constant for calculating a contrast medium amount per weight is displayed. When the operator selects the constant key 426, an input screen is displayed. The constant can be set from that input screen. When a start delay time is set in the injection protocol, the set start delay time is displayed. When the operator selects a delay key, an input screen is displayed. The start delay time can be set from that input screen. When a start delay time is not set, the delay key is not displayed.

In a rate and amount key 428, the injection rate and the injection amount are displayed. When the operator selects the rate and amount key 428, an input screen is displayed. The injection rate and the injection amount can be set from that input screen. In the case of injecting the chemical liquid from only one of two syringes before injecting chemical liquids from two syringes, the rate and amount key 428 is displayed as a bar indicating the injection rate and the injection amount of one of the chemical liquids on the left side (first phase), and as a bar indicating the injection rate and the injection amount of the two chemical liquids on the right side (second phase). Further, a line indicating an injection finish of the chemical liquid is also displayed. A finish time indication 431 is displayed below that line. Because the second phase indication indicates that two chemical liquids are being injected, the second phase indication is displayed in two color gradations, for example, in green and blue. On the other hand, because the first phase indication indicates that one chemical liquid is being injected, the first phase indication is displayed in one color, for example, in blue.

When chemical liquids are to be injected from two syringes 91, a mixing ratio of the two chemical liquids is displayed in a mixing ratio key 490 below the rate and amount key 428. For example, when injecting a contrast medium and a physiological saline, the mixing ratio of the contrast medium and the physiological saline is displayed. When the operator selects the mixing ratio key 490, a mixing ratio adjustment screen (popup 491) illustrated in FIG. 16 is displayed. The mixing ratio can be set from that adjustment screen.

On the adjustment screen illustrated in FIG. 16, the mixing ratio adjustment popup 491 is highlighted, and the buttons other than the popup 491 cannot be operated. On a left side of the popup 491, the injection rate, the injection amount, and the mixing ratio are displayed, and on an upper side, the injection rate, the injection amount, and the mixing ratio of one of the two syringes, for example, a contrast medium are displayed. The operator can set the mixing ratio of the contrast medium in units of 1% by operating an upper side adjustment key 492. On a lower side of the popup 491, the injection rate, the injection amount, and the mixing ratio of the another of the two syringes, for example, a physiological saline are displayed. The operator can set the mixing ratio of the physiological saline in units of 1% by operating a lower side adjustment key 493. Each of the upper side adjustment key 492 and the lower side adjustment key 493 is displayed in one color. For example, the upper side adjustment key 492 may be displayed in green, and the lower side adjustment key 493 may be displayed in blue.

On a right side of the popup 491, a slide bar 494 is displayed. The operator can set the mixing ratio in units larger than the upper side adjustment key 492 or the lower side adjustment key 493, for example, units of 10%, by moving the slide bar 494 up or down. An ENTER key 495 is displayed on a lower portion of the popup 491. When the operator selects the ENTER key 495, the set mixing ratio is settled, and the adjustment screen can be closed. A close key 496 is displayed on a right-side, upper portion of the popup 491. When the operator selects the close key 496, the adjustment screen can be closed. In order to show that two chemical liquids are being injected, a background of the slide bar 494 is displayed in two color gradations, for example, green on the upper side and blue on the lower side.

Referring back to FIG. 15, an expected finish time of the injection of the chemical liquid is displayed on a finish time indication 431. When a count time is set in the injection protocol, an elapsed time from the injection start is displayed in a count key 432. When the operator selects the count key 432, an input screen is displayed. The count time can be set from that input screen. When a count time is not set, the count key 432 is not displayed. A limit value of the injection pressure is displayed in a pressure limit key 433. When the operator selects the pressure limit key 433, an input screen is displayed. The limit value can be set from that input screen.

A syringe remaining amount is displayed in a syringe remaining amount indication 434. When the operator selects a total amount key 435 arranged next to the syringe remaining amount indication 434, the syringe remaining amount is set as the injection amount in the injection protocol. When the remaining amount of the chemical liquid changes under a state in which the total amount key 435 is selected, the injection amounts of the first phase and the second phase of the rate and amount key 428 are also automatically updated so as to track the remaining amount. When the total amount key 435 is selected, the total amount key 435 is highlighted, and changes from gray to green, for example. When the total amount key 435 is again selected under a state in which the total amount key 435 has been selected, the total amount key 435 returns to its original state.

A drip key 436 is displayed at a lower portion of the screen. When the operator selects the drip key 436, a setting screen for a drip time, an interval, and an injection amount at one time, for example, is displayed, and a drip injection may be performed. During a period that the setting screen for the drip time is displayed, other keys cannot be operated. When the total of the injection amount for the drip injection, the injection amount for route verification, and the injection amount for the examination, exceeds the amount of the chemical liquid remaining in the syringe, a warning is displayed. After the injection for the route verification has finished, the drip injection may be performed automatically. When the start button is pressed during the drip injection, the injection for the examination may be started. In this case, the injection for the examination may be started without stopping the drip injection.

The injection screen illustrated in FIG. 17 is displayed when the injection starts. On the injection screen, injection phase information 441 is displayed on a right side of the syringe information 421. Syringe remaining amounts 442 are displayed below the syringe information 421 and the injection phase information 441. The syringe remaining amounts 442 are displayed as an image of a syringe. During a period that the chemical liquids corresponding to the indications are being injected, an animated image representing the fact that an injection is being performed is displayed. The display of the animated image changes corresponding to the remaining amount. As such an animated image, for example, an image of a plurality of water droplets representing the chemical liquid is displayed so as to flow out from the tip of the syringe image. In the case of a mixed injection, images of water droplets flowing out from images of two syringes are displayed so as to merge into a single flow. As a result, the operator can discern the injection state. The injection amount may be displayed as the image of the syringe in place of the syringe remaining amount 442.

A pressure graph 443 is displayed below the syringe remaining amount 442. In the pressure graph 443, the vertical axis represents a pressure value, and the horizontal axis represents time. In the pressure graph 443, a pressure limit value 444 is highlighted, and a line indicating the limit value is displayed on the horizontal axis. Further, an expected time 445 of the injection finish of the chemical liquid is highlighted, and a line indicating the expected time is displayed on the vertical axis. An injection pressure cursor 446 is displayed in the pressure graph 443. The color of the injection pressure cursor 446 changes based on the type of chemical liquid to be injected. For example, the injection pressure cursor 446 is displayed in green when injecting a contrast medium, in blue when injecting a physiological saline, and divided into two colors, namely, blue and green, when injecting both a contrast medium and a physiological saline. As a result, the injection state of the chemical liquid, for example, whether a contrast medium, a physiological saline, or a mixed chemical liquid is being injected, can be identified.

The injection pressure cursor 446 moves with time. When the injection of the chemical liquid finishes, the injection pressure cursor 446 is fixed at the position indicating the finish time. When there has been a switch to injection of another chemical liquid or a mixed injection, another injection pressure cursor 446 is displayed. For example, when performing a mixed injection for the first phase, an injection pressure cursor 446 divided into two colors, namely, blue and green, is displayed. Next, when injecting a physiological saline for the second phase, the injection pressure cursor 446 is fixed at the position corresponding to the finish time of the first phase. Then, a blue injection pressure cursor 446 is newly displayed, and moves with time.

An elapsed time screen illustrated in FIG. 18 is displayed for an injection protocol in which a count time is set. In the elapsed time screen, the syringe remaining amounts 442 are displayed below the syringe information 421. An elapsed time 447 from the injection start is displayed below the syringe remaining amount 442. The elapsed time 447 counts up in units of one second. An injection elapsed time bar 448 is displayed below the elapsed time 447. The indication of injection elapsed time bar 448 is updated such that the injection elapsed time bar 448 lengthens as the elapsed time increases.

The indication of the injection elapsed time bar 448 stops being updated when a set count time is reached. On the other hand, the elapsed time 447 continues to count up even after the count time is reached. When the count time is reached, a return button 449 is displayed. When the operator selects the return button 449, an examination site selection screen is displayed. The elapsed time 447 may also indicate the time by counting down. The indication of the injection elapsed time bar 448 may also be updated such that the injection elapsed time bar 448 becomes shorter as the elapsed time increases.

The present invention has been described with reference to various embodiments. However, the present invention is not limited to those embodiments. The present invention may include inventions that have been modified within the scope of the present invention, and inventions that are equivalent to the present invention. Further, the embodiments and modified examples described above may be appropriately combined within the scope of the present invention.

The injecting apparatus 1 may be configured to transmit to and store in external storage devices, such as a radiology information system (RIS), a picture archiving and communication system (PACS), and a hospital information system (HIS), information on an injection result (injection history) via a network. An ultrasonic sensor, a capacitive sensor, and a magnetic sensor, for example, may be used as a non-contact sensor in place of the optical sensor.

When the rear end detection unit 7 has a high detection accuracy, the injecting apparatus 1 may be configured to stop the pushing unit 4 without moving forward the pushing unit 4 after the rear end detection unit 7 detects the rear end 931 of the syringe 91. In other words, the control unit 50 is configured to move forward the pushing unit 4 during the period that the operator is pressing down the forward movement button 24 on the injection head 2. The rear end detection unit 7 is configured to transmit, when the rear end detection unit 7 detects the rear end 931, a detection signal to the control unit 50. The control unit 50, which has received the detection signal, is configured to then stop the pushing unit 4 without moving forward the pushing unit 4.

More specifically, the control unit 50 is configured to stop the forward movement of the pushing unit 4 at the position at which the rear end detection unit 7 detects the rear end 931. Even in this case, the pushing unit 4 can be stopped without abutting against the rear end 931. An example of a method of increasing the detection accuracy is to provide a diaphragm, e.g., a slit, in the light emitting portion 721 of the rear end detection unit 7 to suppress divergence of the light beams.

The control unit 50 may be configured to calculate the forward movement distance based on the thickness of the rear end 931 of the syringe 91, which is input by the operator, instead of determining the forward movement distance by referring to the data table. Even in such an embodiment, the control unit 50 is capable of acquiring the forward movement distance. The control unit 50 may also be configured to acquire the forward movement distance by the operator inputting the forward movement distance.

Further, instead of the type of the adapter 8 being detected by the adapter detection unit 6, the type of the adapter 8 may be input by the operator. A data carrier in which information on the syringe 91 is stored may be arranged in the syringe 91. In this case, a data table associating the type of the adapter 8 and the information on the syringe 91 is stored in advance in the control unit 50. The control unit 50 may be configured to acquire the type of the adapter 8 by referring to that data table.

The injecting apparatus 1 may be configured to notify, when the rear end 931 is detected before the pushing unit 4 has been moved forward by the estimated distance, the operator of the possibility of an erroneous detection. This enables the operator to be notified even when the rear end detection unit 7 erroneously detects the rear end 931. For example, when the rear end 931 is detected immediately after the pushing unit 4 has stated to move forward, there is a high possibility that the detection is erroneous. In such a case, the injecting apparatus 1 can notify the operator of the possibility of an erroneous detection.

Specifically, the control unit 50 is configured to acquire the estimated distance that the pushing unit 4 is to be moved forward until the rear end 931 is detected. The control unit 50 is configured to notify, when the rear end 931 is detected before the pushing unit 4 has been moved forward by the estimated distance, that there is a possibility of an erroneous detection by using a screen display or a sound. In this case, the estimated distance corresponds to the distance that the pushing unit 4 is to be moved forward until the rear end detection unit 7 detects the rear end 931 of the unused syringe 91. The control unit 50 is capable of acquiring the estimated distance in the same manner as in the second embodiment. Further, the operator may also input to the injecting apparatus 1 a predetermined distance as the estimated distance.

The control unit 50 is configured to determine the estimated distance corresponding to the type of the adapter 8, and to store in the memory unit 53 the distance that the pushing unit 4 actually moved forward during the period that the pushing unit 4 is moving forward. The control unit 50 is also configured to compare the acquired estimated distance and the actually moved forward distance, and when the rear end detection unit 7 detects the rear end 931 before the pushing unit 4 has been moved forward by the estimated distance, to produce a sound or to display an indication on the screen of the console 10 in order to issue a notification of the detection.

The control unit 50 is configured to continue the forward movement of the pushing unit 4 even when the rear end 931 is detected before the pushing unit 4 has been moved forward by the estimated distance. However, the control unit 50 may be configured to stop the forward movement of the pushing unit 4 in addition to issuing a notification of the detection. The control unit 50 may also be configured to reduce the forward movement speed when the rear end 931 is detected before the pushing unit 4 has been moved forward by the estimated distance.

This application claims the benefit of priority from Japanese Patent Application No. 2014-038269, filed on Feb. 28, 2014, the content of which is incorporated herein by reference.

REFERENCE SIGNS LIST

1: injecting apparatus, 2: injection head, 4: pushing unit, 6: adapter detection unit, 7: rear end detection unit, 8: adapter, 21: frame, 24: forward movement button, 50: control unit, 53: memory unit, 61: button, 62: sensor, 83: convex portion, 91: syringe, 611: abutment portion, 721: light emitting portion, 722: light receiving portion, 931: rear end

The invention claimed is:

1. An injecting apparatus for injecting a chemical liquid, the injecting apparatus comprising:
   an injection head to which a syringe filled with the chemical liquid is to be mounted;
   a pushing unit provided on the injection head, pushing a rear end of the syringe, and including an abutment surface to be abutted to the rear end; and
   a rear end detection unit provided on the injection head and detecting the rear end in a state that the pushing unit and the rear end are separated in a contactless manner,
   wherein the rear end detection unit includes a light emitting portion and a light receiving portion, and the light emitting portion and the light receiving portion are held by the pushing unit so as to protrude with respect to the abutment surface.

2. An injecting apparatus for injecting a chemical liquid, the injecting apparatus comprising:
   an injection head to which a syringe filled with the chemical liquid is to be mounted;
   a pushing unit provided on the injection head and pushing a rear end of the syringe;
   a rear end detection unit provided on the injection head and detecting the rear end in a state that the pushing unit and the rear end are separated in a contactless manner;
   a memory storing a forward movement distance that the pushing unit is to be moved forward after the rear end is detected; and
   a control unit configured to control the injection head, the control unit acquiring the forward movement distance, and causing the pushing unit to move forward by the forward movement distance after the rear end is detected and to stop at a position separated from the rear end.

3. An injecting apparatus according to claim 2, wherein the control unit causes the pushing unit to move forward while a forward movement button is pressed down, and when the rear end detection unit detects the rear end while the forward movement button is pressed down, the control unit causes the pushing unit to move forward by the forward movement distance and to stop at the position separated from the rear end.

4. An injecting apparatus according to claim 2, wherein the control unit is capable of increasing a forward movement speed of the pushing unit, and the control unit decreases the forward movement speed when the rear end detection unit detects the rear end while the forward movement speed is being increased.

5. An injecting apparatus according to claim 2, further comprising an adapter configured to mount the syringe to the injection head, wherein the control unit acquires the forward movement distance based on a type of the adapter.

6. An injecting apparatus according to claim 2, further comprising an adapter configured to mount the syringe to the injection head,
   wherein the control unit acquires the forward movement distance based on a type of the adapter and a distance that the pushing unit is to be moved forward until the rear end detection unit detects the rear end.

7. An injecting apparatus for injecting a chemical liquid, the injecting apparatus comprising:
   an injection head to which a syringe filled with the chemical liquid is to be mounted;
   a pushing unit provided on the injection head and pushing a rear end of the syringe;

a rear end detection unit provided on the injection head and detecting the rear end in a state that the pushing unit and the rear end are separated in a contactless manner;

a memory storing an estimated distance corresponding to a distance that the pushing unit is to be moved forward until the rear end detection unit detects the rear end; and a control unit acquiring the estimated distance, and causing the pushing unit to stop when the pushing unit is moved forward by the estimated distance before the rear end is detected.

8. An injecting apparatus for injecting a chemical liquid, the injecting apparatus comprising:

an injection head to which a syringe filled with the chemical liquid is to be mounted;

a pushing unit provided on the injection head, pushing a rear end of the syringe, and including an abutment surface to be abutted to the rear end; and a rear end detection unit provided on the injection head, detecting the rear end in a state that the pushing unit and the rear end are separated in a contactless manner, and arranged to be tilted forward with respect to a perpendicular line of the abutment surface.

\* \* \* \* \*